United States Patent
Nagase et al.

(10) Patent No.: US 8,133,169 B2
(45) Date of Patent: Mar. 13, 2012

(54) IN-VIVO IMAGE ACQUIRING SYSTEM CAPABLE OF CONTROLLING ILLUMINATING UNIT AND DETERMINING WHETHER TO WIRELESSLY TRANSMIT IMAGE INFORMATION BASED ON ESTIMATED DISTANCE

(75) Inventors: Ayako Nagase, Yokohama (JP); Junichi Uchida, Sagamihara (JP)

(73) Assignee: Olympus Medical Systems Corp., Tokyo (JP)

( * ) Notice: Subject to any disclaimer, the term of this patent is extended or adjusted under 35 U.S.C. 154(b) by 817 days.

(21) Appl. No.: 12/234,191

(22) Filed: Sep. 19, 2008

(65) Prior Publication Data
US 2009/0073260 A1  Mar. 19, 2009

(30) Foreign Application Priority Data
Sep. 19, 2007  (JP) .................. 2007-243071

(51) Int. Cl.
*A61B 1/00* (2006.01)
(52) U.S. Cl. ........................ 600/117; 600/112
(58) Field of Classification Search .............. 600/476, 600/115, 118, 176, 127, 167, 117, 112; 348/77
See application file for complete search history.

(56) References Cited

U.S. PATENT DOCUMENTS

| | | | |
|---|---|---|---|
| 7,762,947 B2 | 7/2010 | Honda | |
| 2004/0215059 A1 | 10/2004 | Homan et al. | |
| 2004/0249291 A1 | 12/2004 | Honda et al. | |
| 2006/0184039 A1* | 8/2006 | Avni et al. .................... | 600/476 |
| 2007/0073105 A1 | 3/2007 | Honda | |
| 2007/0161858 A1 | 7/2007 | Homan et al. | |
| 2007/0191677 A1 | 8/2007 | Nishimura et al. | |
| 2008/0033247 A1* | 2/2008 | Wilson et al. ................. | 600/115 |
| 2008/0167523 A1 | 7/2008 | Uchiyama et al. | |
| 2008/0312502 A1* | 12/2008 | Swain et al. .................. | 600/118 |
| 2008/0319267 A1* | 12/2008 | Fujimori ....................... | 600/176 |
| 2009/0018396 A1* | 1/2009 | Takizawa et al. ............. | 600/127 |
| 2009/0192353 A1* | 7/2009 | Segawa ......................... | 600/118 |
| 2009/0281389 A1* | 11/2009 | Iddan ............................ | 600/167 |
| 2009/0318760 A1* | 12/2009 | Pascal et al. .................. | 600/117 |
| 2009/0318761 A1* | 12/2009 | Rabinovitz .................... | 600/118 |
| 2010/0013914 A1* | 1/2010 | Bettesh et al. ................. | 348/77 |

FOREIGN PATENT DOCUMENTS

| | | |
|---|---|---|
| CN | 1777391 A | 5/2006 |
| CN | 1950018 A | 4/2007 |
| JP | 2003-259392 | 9/2003 |
| JP | 2004-154176 | 6/2004 |
| JP | 2004-321605 | 11/2004 |
| JP | 2005-288191 | 10/2005 |
| JP | 2005-319096 | 11/2005 |
| JP | 2006-122502 | 5/2006 |
| WO | 2007/010997 A1 | 1/2007 |

* cited by examiner

*Primary Examiner* — Le Luu
(74) *Attorney, Agent, or Firm* — Scully, Scott, Murphy & Presser, P.C.

(57) ABSTRACT

An in-vivo image acquiring apparatus includes an imaging unit which is introduced inside a subject and picks up image information inside the subject, an illuminating unit which illuminates an imaging portion imaged by the imaging unit, a transmission processing unit which performs a process to wirelessly transmit the image information acquired by the imaging unit to an external apparatus. A light-control unit determines light-control amount information based on brightness of the image information acquired by the imaging unit, and performs a control of light control of the illuminating unit according to the light-control amount information. Further, the transmission processing unit performs a process to wirelessly transmit the image information acquired by the imaging unit along with the light-control amount information used for the control of light-control.

17 Claims, 18 Drawing Sheets

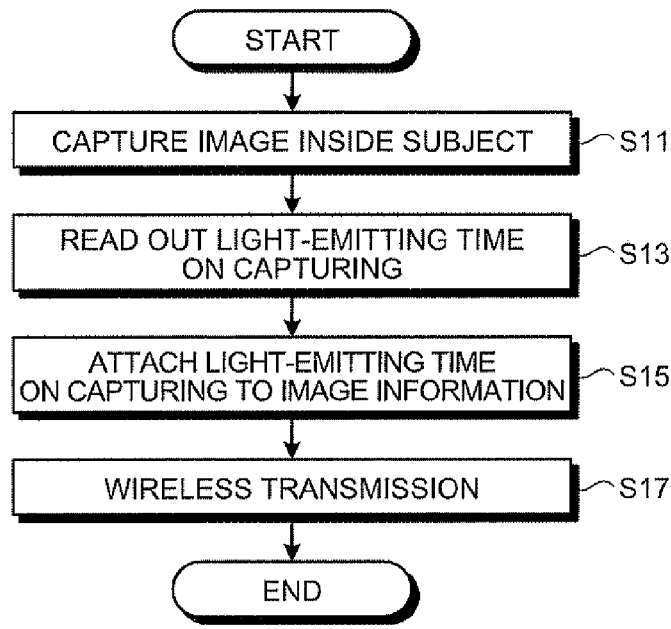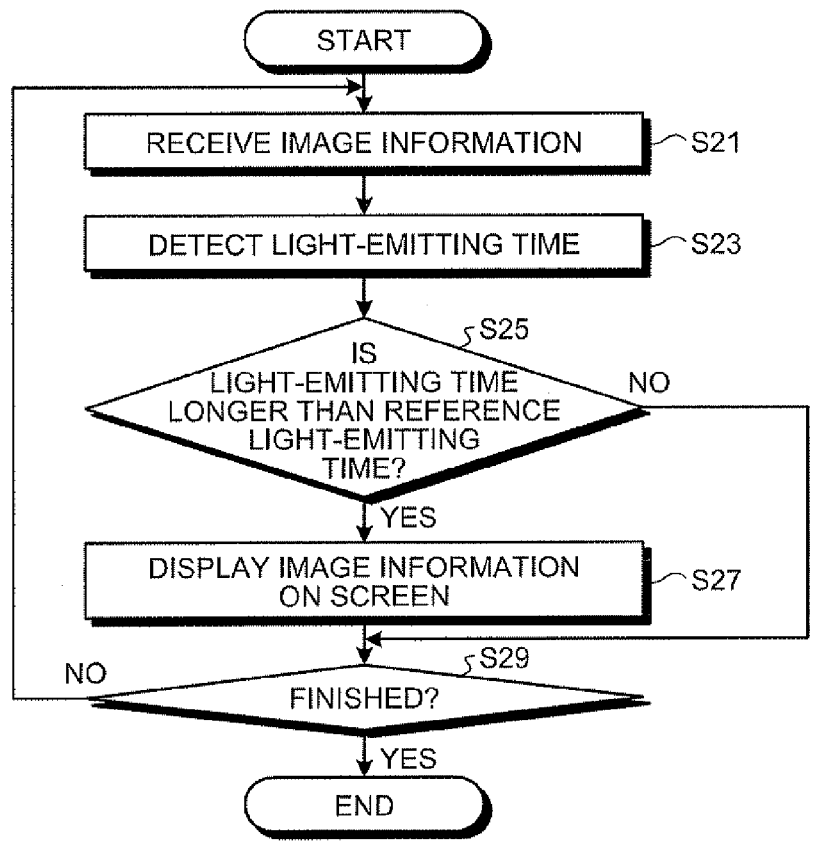

FIG.9

| FRAME | LENGTH OF LIGHT-EMITTING TIME ON CAPTURING COMPARED TO REFERENCE LIGHT-EMITTING TIME | DISPLAY/NONDISPLAY |
|---|---|---|
| 1 | SHORT | NONDISPLAY |
| 2 | SHORT | NONDISPLAY |
| 3 | SHORT | DISPLAY |
| 4 | LONG | DISPLAY |
| 5 | LONG | DISPLAY |
| ⋮ | ⋮ | ⋮ |

IN-VIVO IMAGE ACQUIRING SYSTEM CAPABLE OF CONTROLLING ILLUMINATING UNIT AND DETERMINING WHETHER TO WIRELESSLY TRANSMIT IMAGE INFORMATION BASED ON ESTIMATED DISTANCE

CROSS-REFERENCE TO RELATED APPLICATIONS

This application is based upon and claims the benefit of priority from Japanese Patent Application No. 2007-243071, filed Sep. 19, 2007, the entire contents of which are incorporated herein by reference.

BACKGROUND OF THE INVENTION

1. Field of the Invention

The present invention relates to an in-vivo image acquiring apparatus which is introduced inside a subject to acquire image information inside the subject, an in-vivo image receiving apparatus which receives the image information acquired by the in-vivo image acquiring apparatus, and an in-vivo image acquiring system using the in-vivo image acquiring apparatus.

2. Description of the Related Art

In recent years, a swallowable capsule endoscope has been proposed in a field of endoscope. The capsule endoscope contains inside a capsule-shaped case an imaging unit which acquires image information inside a subject, an illuminating unit which illuminates a portion imaged by the imaging unit, a transmission unit which wirelessly transmits the image information inside the subject, and the like. The capsule endoscope is swallowed by the subject, i.e., a patient from a mouth and introduced inside the subject to examine the subject. The capsule endoscope moving with peristalsis picks up intracelomic images inside organs such as an esophagus, a stomach, a small intestine, and a large intestine until naturally excreted, and wirelessly transmits the acquired image information to an outside. Further, various technologies for the capsule endoscope have been disclosed. For example, there is a known technology where intensity and time of illumination is changed to be suitably adjusted for an amount of reflected light of illumination light emitted by the illuminating unit, whereby a dynamic range of an apparatus is expanded (Japanese Patent Application Laid-Open: 2005-288191).

SUMMARY OF THE INVENTION

An in-vivo image acquiring apparatus according to one aspect of the present invention includes, an imaging unit, which is introduced inside a subject to acquire image information of the subject, an illuminating unit, which illuminates a portion imaged by the imaging unit, a transmission processing unit, which performs a process to wirelessly transmit the image information acquired by the imaging unit to an external apparatus, and a light-control unit, which determines light-control amount information based on brightness of the image information acquired by the imaging unit to perform a light control of the illuminating unit using the light-control amount information, the transmission processing unit performing a process to wirelessly transmit the image information acquired by the imaging unit along with the light-control information used for the light control.

An in-vivo image acquiring apparatus according to another aspect of the present invention includes an imaging unit, which is introduced inside a subject to acquire image information of the subject, an illuminating unit, which illuminates a portion imaged by the imaging unit, a transmission processing unit, which performs a process to wirelessly transmit the image information acquired by the imaging unit to an external device, a light-control unit, which determines light-control amount information based on brightness of the image information acquired by the imaging unit to perform a light control of the illuminating unit using the light-control amount information, and a transmission determination unit, which determines, based on the light-control amount information used for the light control, whether the process to transmit the image information acquired by the imaging unit is to be performed, the transmission determination unit performing a process to wirelessly transmit the image information determined to be transmitted by the transmission determination unit.

An in-vivo image acquiring apparatus according to still another aspect of the present invention includes an imaging unit, which is introduced inside a subject to acquire image information of the subject, an illuminating unit, which illuminates a portion imaged by the imaging unit, a transmission processing unit, which performs a process to wirelessly transmit the image information acquired by the imaging unit to an external device, a light-control unit, which determines light-control amount information based on brightness of the image information acquired by the imaging unit to perform a light control of the illuminating unit, and an image processing unit, which performs, based on the light-control amount information used for the light control, a predetermined image processing on the image information acquired by the imaging unit.

An in-vivo image receiving apparatus according to still another aspect of the present invention receives image information transmitted wirelessly from an in-vivo image acquiring apparatus including an imaging unit, which is introduced inside a subject to acquire image information of the subject, an illuminating unit, which illuminates a portion imaged by the imaging unit, a transmission processing unit, which performs a process to wirelessly transmit the image information acquired by the imaging unit to an external device, a light-control unit, which determines light-control amount information based on brightness of the image information acquired by the imaging unit to perform a light control of the illuminating unit using the light-control amount information, the transmission processing unit performing a process to wirelessly transmit the image information acquired by the imaging unit along with the light-control information used for the light control, the in-vivo image receiving apparatus. The in-vivo image receiving apparatus includes a receiving unit, which is arranged outside the subject, and receives the image information and the light-control information transmitted wirelessly from the in-vivo image acquiring apparatus and a display processing unit, which performs, based on the light-control amount information received along with the image information by the receiving unit, a process to display the image information.

An in-vivo image receiving apparatus according to still another aspect of the present invention receives image information transmitted wirelessly from an in-vivo image acquiring apparatus including an imaging unit, which is introduced inside a subject to acquire image information of the subject, an illuminating unit, which illuminates a portion imaged by the imaging unit, a transmission processing unit, which performs a process to wirelessly transmit the image information acquired by the imaging unit to an external device, a light-control unit, which determines light-control amount information based on brightness of the image information acquired by the imaging unit to perform a light control of the illuminating unit using the light-control amount information, and a transmission determination unit, which determines, based on the light-control amount information used for the light control, whether the process to transmit the image information acquired by the imaging unit is to be performed, the transmission determination unit performing a process to wirelessly transmit the image information which is determined to be transmitted by the transmission determination unit. The in-vivo image receiving apparatus includes a receiving unit, which is arranged outside the subject, and receives the image information and the light-control information transmitted wirelessly from the in-vivo image acquiring apparatus, and a display processing unit, which performs, based on the light-control amount information received along with the image information by the receiving unit, a process to display the image information.

An in-vivo image receiving apparatus according to still another aspect of the present invention receives image information transmitted wirelessly from an in-vivo image acquiring apparatus including an imaging unit, which is introduced inside a subject to acquire image information of the subject, an illuminating unit, which illuminates a portion imaged by the imaging unit, a transmission processing unit, which performs a process to wirelessly transmit the image information acquired by the imaging unit to an external device, a light-control unit, which determines light-control amount information based on brightness of the image information acquired by the imaging unit to perform a light control of the illuminating unit, and an image processing unit, which performs, based on the light-control amount information used for the light control, a predetermined image processing on the image information acquired by the imaging unit. The in-vivo image receiving apparatus includes a receiving unit, which is arranged outside the subject, and receives the image information and the light-control information transmitted wirelessly from the in-vivo image acquiring apparatus, and a display processing unit, which performs, based on the light-control amount information received along with the image information by the receiving unit, a process to display the image information.

An in-vivo image acquiring system according to still another aspect of the present invention includes an in-vivo image acquiring apparatus including an imaging unit, which is introduced inside a subject to acquire image information of the subject, an illuminating unit, which illuminates a portion imaged by the imaging unit, a transmission processing unit, which performs a process to wirelessly transmit the image information acquired by the imaging unit to an external device, a light-control unit, which determines light-control amount information based on brightness of the image information acquired by the imaging unit to perform a light control of the illuminating unit using the light-control amount information, the transmission processing unit performing a process to wirelessly transmit the image information acquired by the imaging unit along with the light-control information used for the light control, a receiving unit, which is arranged outside the subject, and receives the image information and the light-control information transmitted wirelessly from the in-vivo image acquiring apparatus, and a display processing unit, which performs, based on the light-control amount information received along with the image information by the receiving unit, a process to display the image information.

Further, an in-vivo image acquiring system according to still another aspect of the present invention includes an in-vivo image acquiring apparatus including an imaging unit, which is introduced inside a subject to acquire image information of the subject, an illuminating unit, which illuminates a portion imaged by the imaging unit, a transmission processing unit, which performs a process to wirelessly transmit the image information acquired by the imaging unit to an external device, a light-control unit, which determines light-control amount information based on brightness of the image information acquired by the imaging unit to perform a light control of the illuminating unit using the light-control amount information, and a transmission determination unit, which determines, based on the light-control amount information used for the light control, whether the process to transmit the image information acquired by the imaging unit is to be performed, the transmission determination unit performing a process to wirelessly transmit the image information which is determined to be transmitted by the transmission determination unit, a receiving unit, which is arranged outside the subject, and receives the image information and the light-control information transmitted wirelessly from the in-vivo image acquiring apparatus, and a display processing unit, which performs, based on the light-control amount information received along with the image information by the receiving unit, a process to display the image information.

Further, an in-vivo image acquiring system according to still another aspect of the present invention includes an in-vivo image acquiring apparatus comprising an imaging unit, which is introduced inside a subject to acquire image information of the subject, an illuminating unit, which illuminates a portion imaged by the imaging unit, a transmission processing unit, which performs a process to wirelessly transmit the image information acquired by the imaging unit to an external device, a light-control unit, which determines light-control amount information based on brightness of the image information acquired by the imaging unit to perform a light control of the illuminating unit, and an image processing unit, which performs, based on the light-control amount information used for the light control, a predetermined image processing on the image information acquired by the imaging unit, a receiving unit, which is arranged outside the subject, and receives the image information and the light-control information transmitted wirelessly from the in-vivo image acquiring apparatus, and a display processing unit, which performs, based on the light-control amount information received along with the image information by the receiving unit, a process to display the image information.

The above and other objects, features, and advantages of this invention will be better understood by reading the following detailed description of presently preferred embodiments of the invention, when considered in connection with the accompanying drawings.

BRIEF DESCRIPTION OF THE DRAWINGS

FIG. 7 is a process flowchart of the capsule endoscope according to the first embodiment;

FIG. 8 is a process flowchart of the receiving apparatus according to the first embodiment;

FIG. 9 is an explanatory diagram of an example control of display/nondisplay of image information according to a variation;

DETAILED DESCRIPTION OF THE PREFERRED EMBODIMENTS

Exemplary embodiments of the present invention are described below in detail with reference to the drawings.

Figure 1:
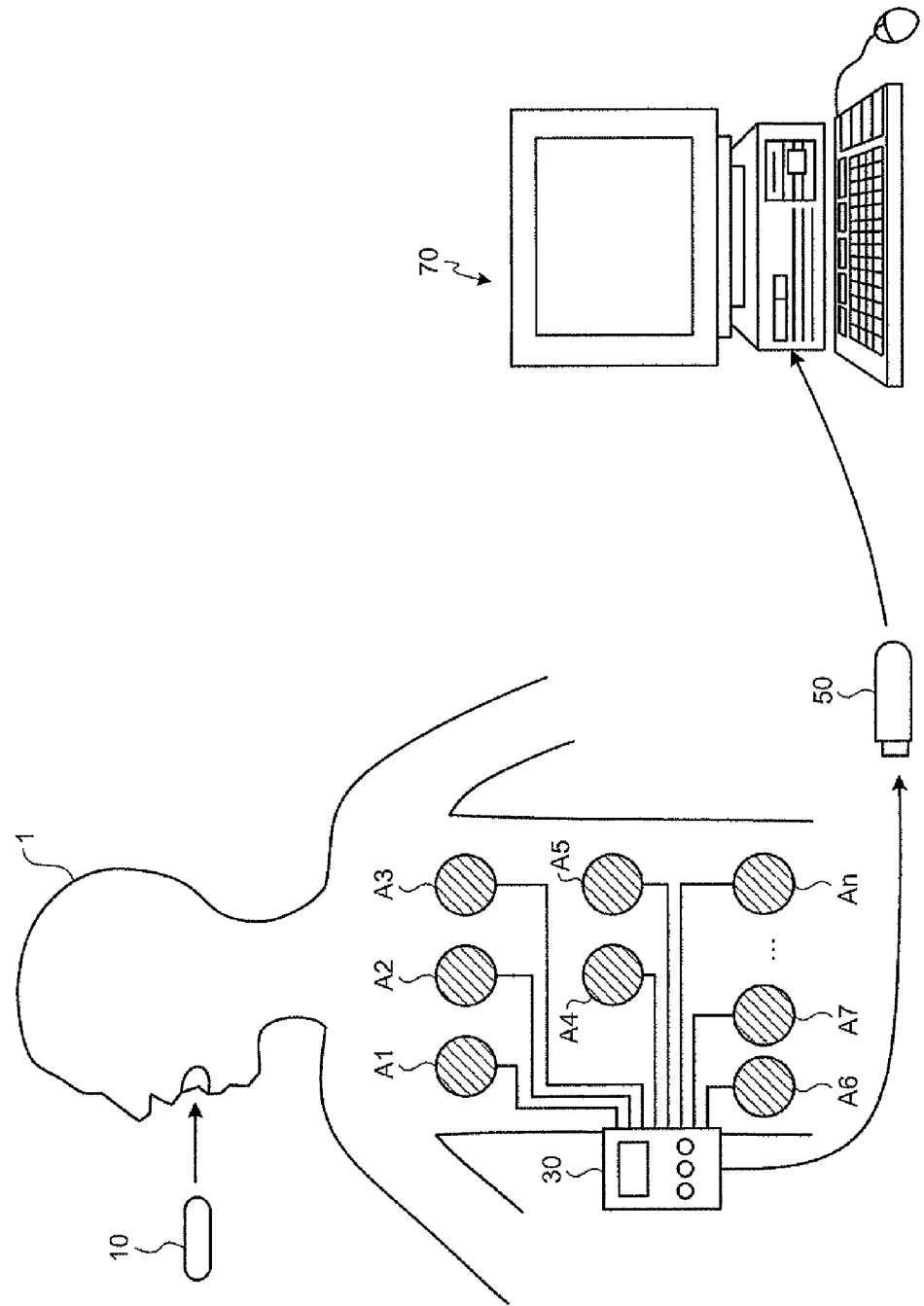
FIG. 1 is a schematic diagram of an overall configuration of an in-vivo image acquiring system according to a first embodiment.

FIG. 1 is a schematic diagram of an overall configuration of an in-vivo image acquiring system according to a first embodiment. As shown in FIG. 1, the in-vivo image acquiring system includes a capsule endoscope 10, a receiving apparatus 30, and a display apparatus 70. The receiving apparatus 30 receives image information which is wirelessly transmitted from the capsule endoscope 10. The display apparatus 70 displays the image information acquired by the capsule endoscope 10 based on the image information received by the receiving apparatus 30. For example, a portable storage medium 50 (portable-storage medium) is used for transmission and reception of the image information between the receiving apparatus 30 and the display apparatus 70.

The capsule endoscope 10 has an imaging function, an illuminating function, and a wireless-transmission function. The capsule endoscope 10 is swallowed from a mouth of a subject 1 and introduced inside the subject 1. The capsule endoscope 10 sequentially picks up intracelomic image information moving inside a body cavity, and wirelessly transmits the acquired image information to an outside.

The receiving apparatus 30 includes plural receiving antennas A1 to An, and receives, via each of the receiving antennas A1 to An, the image information which is wirelessly transmitted from the capsule endoscope 10. In the receiving apparatus 30, a portable storage medium 50, which is a storage medium such as a compact flash (registered trademark), is detachably arranged, and the received image information is stored in the portable storage medium 50 as needed. Thus, the receiving apparatus 30 stores the image information inside the subject 1 acquired by the capsule endoscope 10 in the portable storage medium 50 in order of time.

The receiving antennas A1 to An are realized, for example, by loop antennas, and are dispersedly arranged at predetermined positions on a body surface of the subject 1 as shown in FIG. 1. Specifically, for example, the receiving antennas A1 to An are arranged at positions corresponding to a pathway of the capsule endoscope 10 inside the subject 1. Alternatively, the receiving antennas A1 to An may be dispersedly arranged on a jacket to be worn by the subject 1. In this case, the receiving antennas A1 to An are arranged at the predetermined positions on the body surface of the subject 1 corresponding to the pathway of the capsule endoscope 10 inside the subject 1 as the subject 1 wears the jacket. Further, a number of the receiving antennas are not limited as long as one or more receiving antennas are arranged on the subject 1.

The display apparatus 70 is realized by a general-purpose computer such as a workstation and a personal computer. In the display apparatus 70, the portable storage medium 50 is detachably arranged. The display apparatus 70 reads image information stored in the portable storage medium 50, and displays the read image information on a display such as a Liquid Crystal Display (LCD) and an Electroluminescence Display (ELD). Further, the display apparatus 70 writes information of the subject 1 into the portable storage medium 50 as needed. Further, the display apparatus may be configured to output the image on other mediums via a printer or the like. Further, the display apparatus 70 may be configured to write the image into the storage medium and, in parallel, output the image to a display unit of the receiving apparatus 30. Further, instead of reading the image information from the storage medium, the display apparatus 70 may be configured to output the image information received by the receiving apparatus 30 to a display such as an LCD and an ELD in real time via an insulating part.

Figure 2:
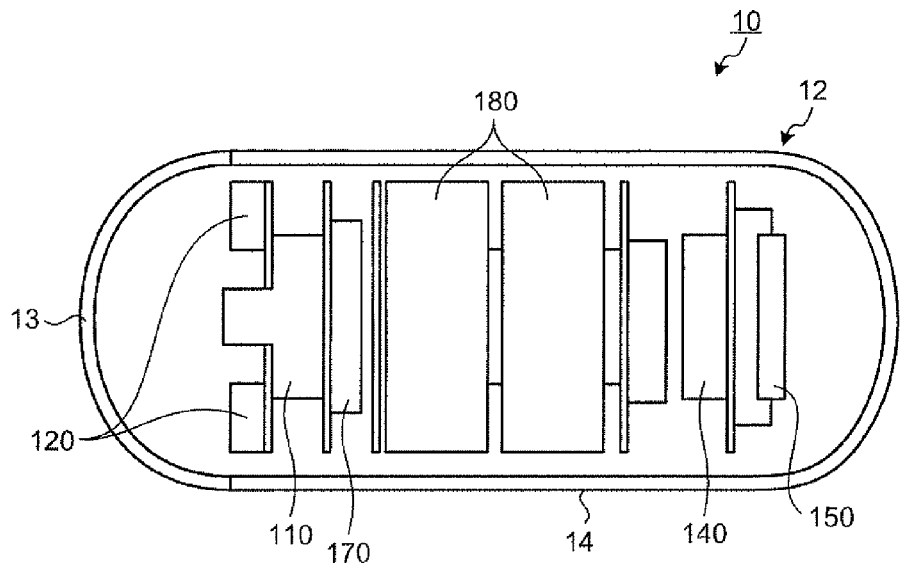
FIG. 2 is a schematic diagram of a configuration of a capsule endoscope according to the first embodiment.

A configuration of the capsule endoscope 10 according to the first embodiment is described below. FIG. 2 is a schematic diagram of the configuration of the capsule endoscope 10. The capsule endoscope 10 contains inside a capsule container 12 an imaging unit 110 which captures an intracelomic image to acquire image information, an illuminating unit 120 which emits illuminating light to an inside of a body cavity, and a transmission processing unit 140, a control unit 170, a power unit 180, and the like. The transmission processing unit 140 performs a process to wirelessly transmit the image information acquired by the imaging unit 110 via a transmission antenna 150. The power unit 180 supplies driving electricity for each unit of the capsule endoscope 10.

The container 12 has a size which can be swallowed by a man or woman, and is formed with a substantially hemispherical front cover 13 and a body cover 14 forming a joint.

The front cover 13 is made of a transparent material and works as an optical window. The imaging unit 110 and the illuminating unit 120 are arranged at positions opposing to the front cover 13 inside the container 12. The front cover 13 allows illuminating light from the illuminating unit 120 to transmit through the front cover 13 to an outside of the container 12, and introduces reflected light thereof to an inside of the container 12.

According to the capsule endoscope 10, illuminating light emitted by the illuminating unit 120 transmits through the front cover 13 to be reflected by a wall surface of organ. Then, the imaging unit 110 receives the reflected light via the front cover 13 and captures an image inside the subject 1. The image information acquired as above is broadly divided into those which are captured when the front cover 13 of the capsule endoscope 10 is close to an inner wall of organ, and those which are captured when the front cover 13 is away from the inner wall of organ.

Figure 3A:
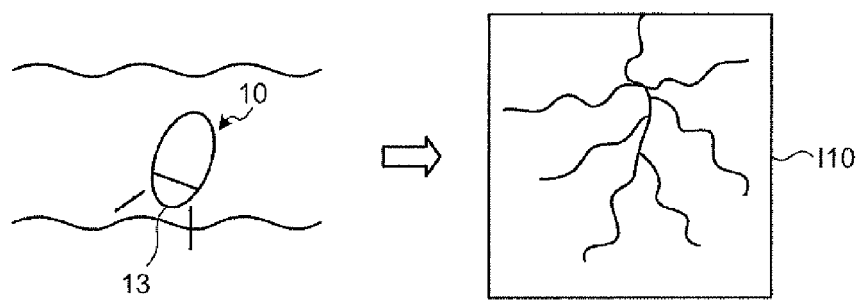
FIG. 3A is an explanatory diagram of an example of an acquired image, and an example of a state of a capsule endoscope.
Figure 3B:
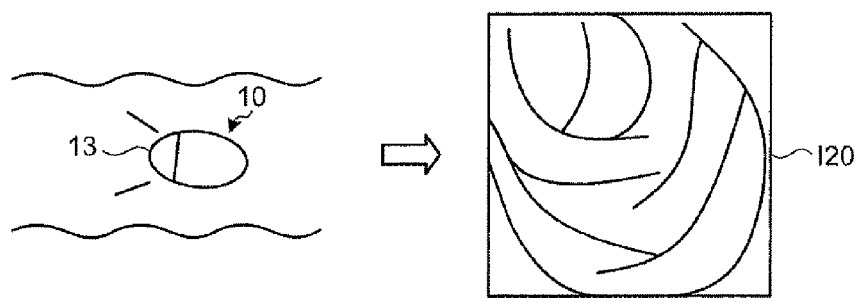
FIG. 3B is an explanatory diagram of an example of an acquired image, and an example state of the capsule endoscope.

FIGS. 3A and 3B are explanatory diagrams of an example state of the capsule endoscope 10 where the capsule endoscope 10 is inside a cavity of a large intestine, and of an example of an acquired image, respectively. In the example shown in FIG. 3A, the capsule endoscope 10 is in a state where the front cover 13 is close to an intestine wall, and a captured image I10 covers only a small limited area of the intestine wall. On the other hand, in the example shown in FIG. 3B, the capsule endoscope 10 is in a state where the front cover 13 is away from an intestine wall and faces in a direction along the cavity, and with an captured image I20, an overview of the cavity can be observed broadly. Thus, the latter is useful, for example, for a screening test and the like.

The image captured when the front cover 13 is close to the wall surface of intestine requires only a small amount of luminescence because the front cover 13 are close to the wall surface of intestine. On the other hand, the image captured when the front cover 13 faces in the direction along the cavity requires a large amount of luminescence because the front cover 13 is away from the wall surface of organ. Thus, distance between the front cover 13 and the wall surface of organ can be estimated based on information of the amount of luminescence of the acquired image, whereby a state of the capsule endoscope 10 can be classified to the state shown in FIG. 3A or the state shown in FIG. 3B. The present embodiment automatically divides the acquired image information as described above, and more specifically, divides the image information based on the amount of luminescence and the light-control amount information.

Figure 4:
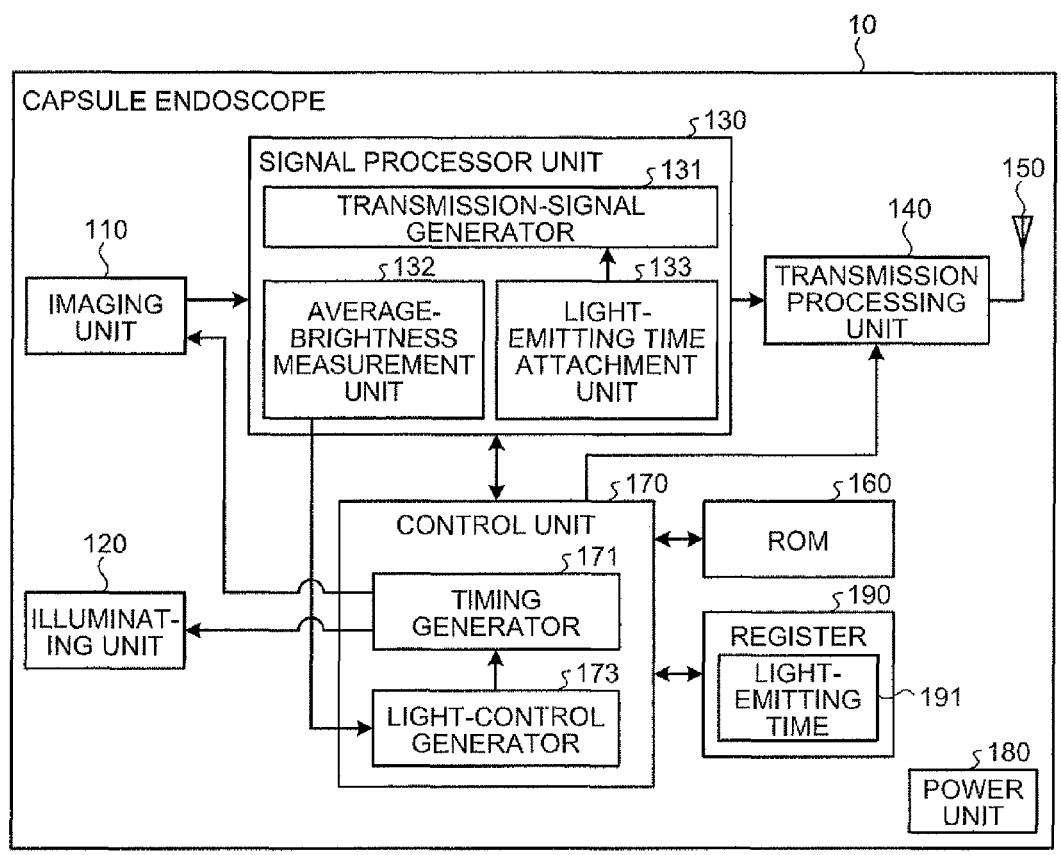
FIG. 4 is a block diagram of a functional configuration of the capsule endoscope according to the first embodiment.

FIG. 4 is a block diagram of a functional configuration of the capsule endoscope 10. As shown in FIG. 4, the capsule endoscope 10 includes the imaging unit 110, the illuminating unit 120, a signal processor 130, the transmission processing unit 140, the transmission antenna 150, a ROM 160, a register 190, the control unit 170, the power unit 180.

The imaging unit 110 includes an imaging device having an image sensor such as a CCD and CMOS, and an imaging lens which forms an image of incident light on the imaging device, and the like. The imaging unit 110 performs an imaging operation which outputs an analog signal corresponding to intensity of the incident light to capture an image inside the subject 1. To give a detailed description, the imaging unit 110 performs the imaging operation at a timing when an imaging-unit-driving pulse is supplied from a timing generator 171 which is described later.

The illuminating unit 120 includes a light-emitting device such as a LED, and a driving circuit of the light-emitting device. The illuminating unit 120 performs an illuminating operation to emit illuminating light and to illuminate a portion imaged by the imaging unit 110. To give a detailed description, the illuminating unit 120 starts the illuminating operation at a timing when an illuminating-unit driving pulse is supplied from the timing generator 171, and emits illuminating light for a light-emitting time corresponding to a pulse duration of the supplied illuminating-unit driving pulse.

The signal processor 130 includes a transmission-signal generator 131, an average-brightness measurement unit 132, and a light-emitting time attachment unit 133.

The transmission-signal generator 131 performs an analog-signal process such as a color-balance adjustment and a gamma control on an analog signal which is input from the imaging unit 110, and then converts the analog signal into a digital signal. Based on the acquired digital signal, the transmission-signal generator 131 generates a transmission signal to be used for wirelessly transmitting the acquired image information to an outside. For example, with a frame representing information of a piece of image, the transmission-signal generator 131 attaches a vertical synchronizing signal to a head of the frame, and attaches a horizontal synchronizing signal to each head of constituent data of each line to thereby generate a transmission signal, and outputs the transmission signal to the transmission processing unit 140.

Figure 5:
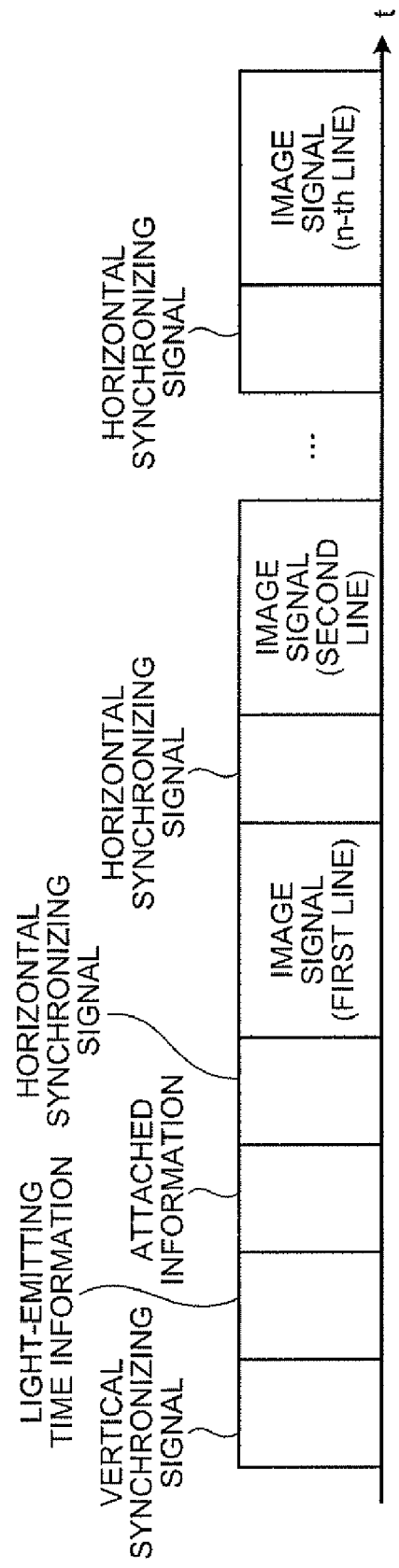
FIG. 5 is a diagram of an example of a transmission signal generated by a transmission-signal generator.

FIG. 5 is a diagram of an example of a transmission signal generated by the transmission-signal generator 131. As shown in FIG. 5, the transmission signal is formed as the vertical synchronizing signal, fields of light-emitting time and attached information, and constituent data of each line including the horizontal synchronizing signal. The light-emitting time information is input from the light-emitting time attachment unit 133 described later. The attached information is, for example, information such as a model or a serial number of the capsule endoscope, and white balance coefficient. The transmission signal is input into the transmission processing unit 140, and is wirelessly transmitted to the receiving apparatus 30 outside a body. The receiving apparatus 30 receiving the transmission signal detects a head part of an image via the vertical synchronizing signal, and a head of an image signal of each line via the horizontal synchronizing signal to thereby process each image signal and to acquire image information.

The average-brightness measurement unit 132 measures an average brightness value of the acquired image information. Specifically, with a light-control area for a measurement previously set, the average-brightness measurement unit 132 calculates a weighted average value of RGB values of each pixel forming the light-control area, and acquires an average brightness of the light control area. The measured average brightness value is output to a light-control unit 173 described later. Alternatively, a whole area of the acquired image information may be measured to measure the average brightness value.

Light-emitting time calculated by the light-control unit 173 described later is input to a register. The light-emitting time attachment unit 133 outputs the input light-emitting time to the transmission-signal generator 131 so that the light-emitting time is attached to the transmission signal generated by the transmission-signal generator 131. Thus, light-emitting time of the illuminating unit 120 on capturing is attached to the acquired image information.

The transmission processing unit 140 is formed by a wireless-transmission circuit and the like which generate a wireless-transmission signal performing a modulation process and the like on the transmission signal input from the transmission signal generator 131 as needed. The transmission processing unit 140 performs a process to wirelessly transmit the generated transmission signal to an outside via the transmission antenna 150.

The ROM 160 stores therein various data such as a serial number and a white balance coefficient needed for an operation of the capsule endoscope 10. The register 190 stores therein light-emitting time 191 calculated by the light-control unit 173 described later. Alternatively, a RAM may be used instead of the register 190.

The control unit 170 controls each unit forming the capsule endoscope 10, and controls the entire operation of the capsule endoscope 10 extensively. The control unit 170 includes the timing generator 171 and the light-control unit 173.

The timing generator 171 sets driving timing of the imaging unit 110 and the illuminating unit 120, and controls the imaging operation of the imaging unit 110 and the illuminating operation of the illuminating unit 120. For example, an imaging-unit-driving pulse is supplied for the imaging unit 110 at intervals of 0.5 seconds to control the imaging operation of the imaging unit 110, and an illuminating-unit-driving pulse is supplied for the illuminating unit 120 just before the supply of the imaging start pulse to control the illuminating operation of the illuminating unit 120. Further, the timing generator 171 increases or decreases a pulse amplitude of the illuminating-unit-driving pulse based on the light-emitting time which is input from the light-control unit 173, and determines a start timing of operation at a rising of the pulse and a termination timing of operation at a falling of the pulse. Then, the timing generator 171 drives each unit forming the signal processor 130 based on the timing of supply of the imaging-unit-driving pulse to thereby synchronize each process with the timing of supply of the imaging-unit-driving pulse.

The light-control unit 173 determines light-control-amount information based on brightness of the image information acquired by the imaging unit 110, and performs a light-control control of the illuminating unit 120. Specifically, the light-control unit 173 compares an average value which is input from the average-brightness measurement unit 132 with a reference brightness value previously set as a reference brightness value, and determines the brightness of the light-control area of the acquired image information. The reference brightness value has for example, a brightness value with which a user can easily view a content of the image. Further, the light-control unit 173 calculates, for example, light-emitting time of the illuminating unit 120 based on the comparison result as light-control information, and outputs the calculated light-emitting time to the timing generator 171. Thus, the light-emitting time of the illuminating unit 120 is calculated based on the brightness of the light-control area in the acquired image information, and in a following imaging operation, the illuminating unit 120 emits illuminating light according to the light-emitting time, whereby quality of captured images is stably maintained. For example, when the brightness value of the captured image is larger than the reference brightness value, the light-emitting time of the illuminating unit 120 is set short in the following operation, whereas when the brightness value of the captured image is smaller than the reference brightness value, the light-emitting time of the illuminating unit 120 is set long in the following operation. Further, the light-control amount information is not limited to the light-emitting time. For example, an electricity value supplied for a light-emitting device forming the illuminating unit 120 may be modulated as the light-control amount information. Further, a gain of the output signal of an imaging device again may be modulated as the light-control amount information.

Further, light-emitting time calculated by the light-control unit 173 is output to the light-emitting time attachment unit 133 based on a supply timing of the following imaging-unit-driving pulse by the control unit 170. Then, the imaging unit 110 the image information acquired by the imaging unit 110 is wirelessly transmitted to the receiving apparatus 30 along with the light-emitting time of the illuminating unit 120 in the capturing.

Figure 6:
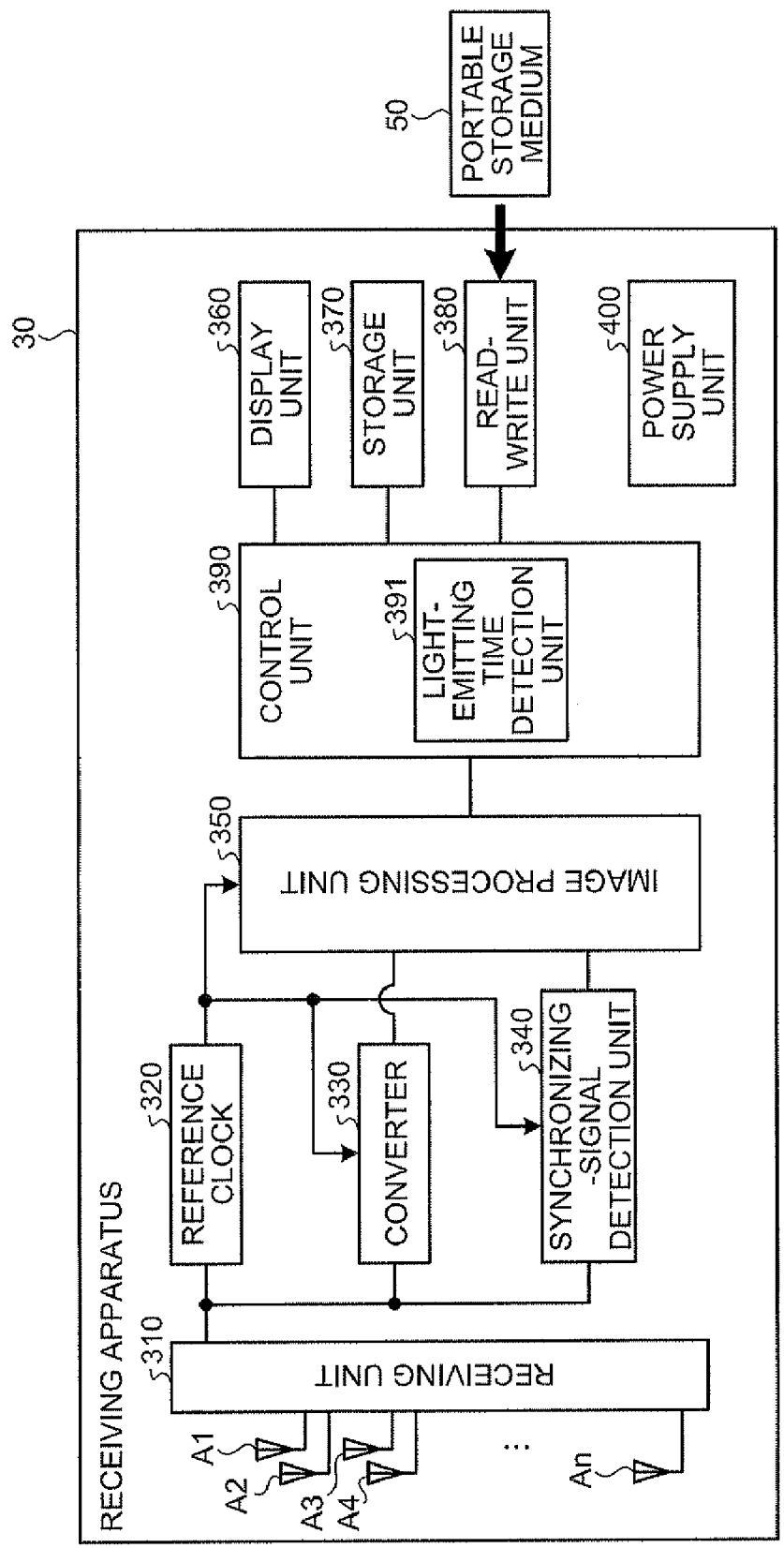
FIG. 6 is a block diagram of a functional configuration of a receiving apparatus according to the first embodiment.

A configuration of the receiving apparatus 30 which receives the image information wirelessly transmitted by the capsule endoscope 10 is described below. FIG. 6 is a block diagram of a functional configuration of the receiving apparatus 30. As shown in FIG. 6, the receiving apparatus 30 includes antennas A1 to An, a receiving unit 310, a reference clock 320, a converter 330, a synchronizing-signal detection unit 340, an image processing unit 350, a display unit 360, a storage unit 370, a read-write unit 380, a control unit 390, and a power supply unit 400. The power supply unit 400 supplies driving electricity for each unit forming the receiving apparatus 30.

The receiving unit 310 receives a wireless-transmission signal from the capsule endoscope 10 via receiving antennas A1 to An. Specifically, the receiving unit 310, under a control by the control unit 390, switches a receiving antenna to receive the wireless-transmission signal from the capsule endoscope, to any of the receiving antennas A1 to An. More specifically, the switching of the receiving antennas is performed as each of the receiving antennas A1 to An detects a reception intensity of the wireless-transmission signal from the capsule endoscope 10, and the control unit 390 performs a control to switch a receiving antenna to a receiving antenna with the highest reception intensity of wireless transmission signals. Then, the receiving unit 310 performs a demodulation process on a wireless-transmission signal from the capsule endoscope 10 via the switched receiving antenna to thereby demodulate the wireless-transmission signal to be an image signal. The image signal corresponds to the transmission signal generated by the capsule endoscope 10. The image signal includes the image information acquired by the capsule endoscope 10, a vertical synchronizing signal contained in each frame, a horizontal synchronizing signal contained in each line of a frame, light-emitting time information, and attached information.

The reference clock 320 outputs a clock signal which works as a reference of a process performed on a wireless-transmission signal from the capsule endoscope 10. The converter 330 performs a serial/parallel conversion process on the image signal demodulated by the receiving unit 310. The synchronizing-signal detection unit 340 detects the vertical synchronizing signal contained in the demodulated image signal for each framer and instructs a timing of an image processing of the image processing unit 350. The image processing unit 350 performs a predetermined image processing on the demodulated image signal, processes the image signal to a desired format, and outputs the same to the control unit 390.

The display unit 360 displays an image received by the capsule endoscope 10, a name of patient, and the like on screen, and is realized, for example, by a small LCD, a small ELD, or the like.

The storage unit 370 is realized by a variety of IC memories such as a ROM and a RAM of re-writable flash memories or the like. The storage unit 370 stores therein a program for operations of the receiving apparatus 30, programs for realizing various functions of the receiving apparatus 30, data for processing the programs, and the like.

In the read-write unit 380, the portable storage medium 50 is detachably arranged. The read-write unit 380 sequentially stores image information on which the image processing has been performed by the image processing unit 350. The read-write unit 380 is realized by a read-write apparatus suitable for a type of the portable storage medium 50.

The control unit 390 sends instructions for each unit forming the receiving apparatus 30, and performs data transfer, and the like based on the program, data and the like stored in the storage unit 370, and broadly controls the overall operations of the receiving apparatus 30. The control unit 390 includes a light-emitting time detection unit 391. The light-emitting time detection unit 391 detects, based on the light-emitting time information received along with the image information processed by the image processing unit 350, light-emitting time of the illuminating unit 120 at the time of capturing of image information.

The control unit 390 displays the image information, which is received by the receiving unit 310 and is processed by the image processing unit 350, on the display unit 360, and performs a process to switch and continuously display the image information in order of reception. Then, along with the displaying, the control unit 390 determines display/nondisplay of the image information based on the light-emitting time detected by the light-emitting time detection unit 391. For example, the determination is performed based on whether the detected light-emitting time is longer than reference light-emitting time previously set as a threshold value. As shown in FIG. 3A, the reference light-emitting time is previously set at a value to determine whether the image is one captured when the front cover 13 of the capsule endoscope 10 is close to the wall surface of organ such as a intestine wall as shown in FIG. 3A, or whether the image is one captured when the front cover 13 is away from the wall surface of organ as shown in FIG. 3B. When the image information is determined to be displayed, the control unit 390 performs a process to display the image information on screen of the display unit 360. Further, the control unit 390 may perform a control to fast-forward and change the display time depending on when the light-emitting time of the image information at the time of capturing is longer than the reference light-emitting time, or, equal to or shorter than the reference light-emitting time. For example, when the light-emitting time of the image information at the time of capturing is longer than the reference light-emitting time, the display time of the image information is set longer than a case when the light-emitting time of the image information at the time of capturing is equal to or shorter than the reference light-emitting time. Thus, the control unit 390 performs a process to display the image information to be displayed on screen for display time corresponding to the light-emitting time at the time of acquisition.

Further, the control unit 390 controls the read-write unit 380 to sequentially stores in the portable storage medium 50 image information processed by the image processing unit 350 in correspondence with the light-emitting time information received along with the image information. The control unit 390 may be configured to store only the image information whose light-emitting time at the time of capturing is longer than the reference light-emitting time, and not the image information whose light-emitting time at the time of capturing is equal to or shorter than the reference light-emitting time.

Then, the image information stored in the portable storage medium 50 is read by the display apparatus 70, and displayed on screen of a display. Further, when the display apparatus 70 displays the image information on screen, processes may be performed similarly to the processes according to the screen display of the image information by the receiving apparatus 30. In this case, the display/nondisplay of the image information is determined based on the light-emitting time information stored in the portable storage medium 50 in correspondence with the image information to be displayed. Specifically, the determination is performed based on whether the detected light-emitting time is longer than the reference light-emitting time which is previously set as the threshold value. Further, when the image information is determined to be displayed, the process of the screen display is performed via the display.

Next, an operational procedure of the capsule endoscope 10 and the receiving apparatus 30 according to the first embodiment is described below. FIG. 7 is an operational flowchart of the capsule endoscope 10 according to the transmission of the acquired image information. Firstly, in the capsule endoscope 10, the imaging unit 110 captures an inside of the subject 1 (Step S11). Then, the transmission-signal generator 131 generates a transmission signal based on the acquired image information. On the other hand, the light-emitting time attachment unit 133 reads the light-emitting time 191 stored in the register 190 via the control unit 170 (Step S13), and attaches the light-emitting time 191 to the transmission signal to thereby attach the light-emitting time of the illuminating unit 120 at the time of capturing to the acquired image information (Step S15). Then, the transmission processing unit 140 performs a process to wirelessly transmit the transmission signal input from the transmission-signal generator 131 to an outside of a body (Step S17).

Further, FIG. 8 is an operational flowchart of the receiving apparatus 30 according to the screen display of the acquired image information. In the receiving apparatus 30, firstly, the receiving unit 310 receives the wireless-transmission signal from the capsule endoscope 10 (Step S21). The wireless-transmission signal is demodulated to an image signal by the receiving unit 310. Then, the light-emitting time detection unit 391 identifies light-emitting time information contained in the image signal, and detects the light-emitting time of the illuminating unit 120 at the time of capturing (Step S23). Further, the control unit 390 compares the light-emitting time detected by the light-emitting time detection unit 391 to the reference light-emitting time. If the detected light-emitting time is longer than the reference light-emitting time as a result of the comparison (Step S25: Yes), the control unit 390 performs a process to display the image information on a screen of the display unit 360 (Step S27). On the other hand, if the detected light-emitting time is equal to or shorter than the reference light-emitting time (Step S25: No), the control unit 390 proceeds to Step S29. At Step S29, until the control unit 390 finishes receiving the image information (Step S29: No), the control unit 390 returns to Step S21 and repeats the processes above. Thus, the control unit 390 sequentially displays image information which is wirelessly transmitted from the capsule endoscope 10, and whose light-emitting time at the time of capturing is longer than the reference light-emitting time, on the screen of the display unit 360.

According to the first embodiment described above, the capsule endoscope 10 can acquire the light-emitting time of the illuminating unit 120 at the time of capturing as information from which distance between a head part of the front cover 13 and the wall surface of organ to be captured can be estimated. Further, the light-emitting time information can be attached to the image information and wirelessly transmitted to the receiving apparatus 30. data and the like stored in the storage unit 370. On the other hand, the receiving apparatus 30 compares the light-emitting time at the time of capturing to the reference light-emitting time. Thus, the received image information can be divided to those which are captured when the head of the front cover 13 of the capsule endoscope 10 is close to the wall surface of organ such as an intestine wall, and those which are captured when the head of the front cover 13 away from the wall surface of organ. Then, based on the result of division, only the image information captured when the front cover 13 is close to the wall surface of organ can be displayed on screen. Therefore, the image information which needs to be checked for a screening test and the like can be automatically extracted, whereby the observer can shorten observation time, and avoid burden on visually dividing the image information.

Further, in the light-control control by the light-control unit 173, when there is great difference between the light-emitting amount acquired last time and the light-emitting amount acquired this time, convergence time of the light-control may become long. The convergence time may be used for controlling the display/nondisplay of the image information. FIG. 9 is an explanatory diagram of a example control of the display/nondisplay of the image information. In the example shown in FIG. 9, the light-emitting time at the time of capturing is determined to longer than the reference light-emitting time in frames 4 and 5, and the image information of the frames 4 and 5 is displayed on screen. On the other hand, in the frames 1 to 3, the light-emitting time at the time of capturing is determined to be shorter than reference light-emitting time. Image information of the frames 1 and 2 are not displayed while image information of the frame 3 is displayed considering the convergence time.

Further, distance between the head part of the front cover 13 of the capsule endoscope 10 and the wall surface of organ may be calculated based on the light-emitting time at the time of capturing. The image information may be divided based on this calculated estimated distance. Further, the receiving apparatus 30 may display the calculated estimated distance on screen along with the received image information. Further, distance between the head part of the front cover 13 and the wall surface of organ may be calculated inside the capsule endoscope 10, or may be calculated inside the receiving apparatus 30. When the distance is calculated inside the capsule endoscope, the transmission signal including information of the calculated estimated distance is wirelessly transmitted to the receiving apparatus 30.

Figure 10:
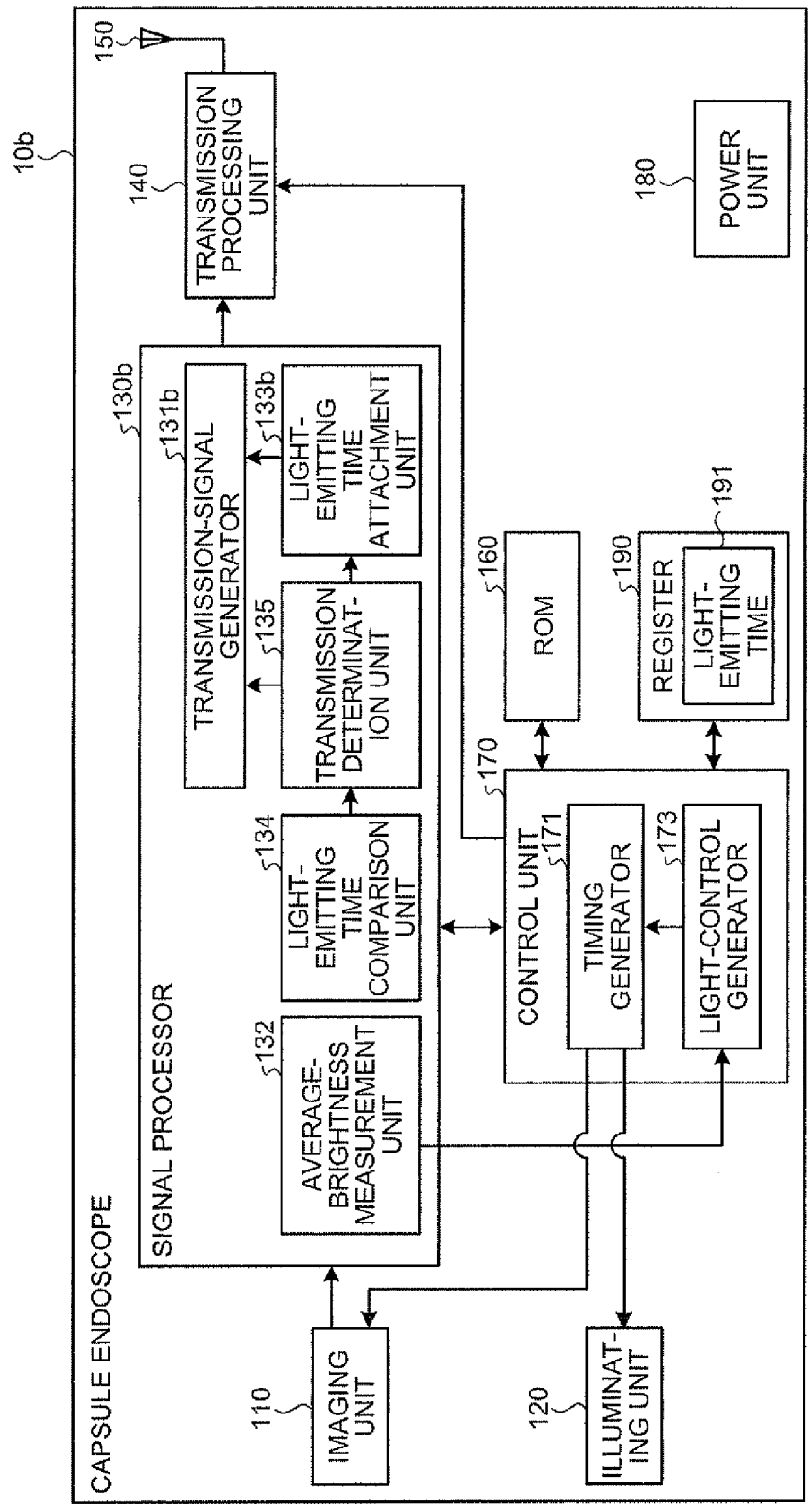
FIG. 10 is a block diagram for explaining a functional configuration of a capsule endoscope according to a second embodiment.

Next, a second embodiment is described below. FIG. 10 is a block diagram of a functional configuration of a capsule endoscope 10*b* according to the second embodiment. Same numerals are attached to components which are identical to the components of the first embodiment.

As shown in FIG. 10, the capsule endoscope 10*b* includes a signal processor 130*b* which is formed by a transmission-signal generator 131*b*, an average-brightness measurement unit 132, a light-emitting time comparison unit 134, and a transmission determination unit 135, a light-emitting time attachment unit 133*b*. The transmission-signal generator 131*b* generates a transmission signal to wirelessly transmit the image information which is determined to be transmitted by the transmission determination unit 135 described later of the acquired image information to an outside of body. The transmission-signal generator 131*b* attaches light-emitting time input by the light-emitting time attachment unit 133*b* to the generated transmission signal. The transmission signal is wirelessly transmitted to the outside of body by the transmission processing unit 140, whereby the acquired image information is wirelessly transmitted to the receiving apparatus 30. On the other hand, the transmission-signal generator 131*b* does not generate a transmission signal for the image information which is determined not to be transmitted by the transmission determination unit 135.

For the light-emitting time comparison unit 134, light-emitting time 191 is input into a register 190 via a control unit 170. The light-emitting time comparison unit 134 compares the input light-emitting time to the reference light-emitting time, and outputs the comparison result to the transmission determination unit 135.

The transmission determination unit 135 determines, based on the comparison result input by the light-emitting time comparison unit 134, whether the image information is to be transmitted. Specifically, the transmission determination unit 135 determines that the image information is to be transmitted when the light-emitting time of the illuminating unit 120 at the time of capturing is longer than the reference light-emitting time as a result of the comparison by the light-emitting time comparison unit 134. On the other hand, the transmission determination unit 135 determines that the image information is not to be transmitted when the light-emitting time of the illuminating unit 120 at the time of capturing is equal to or shorter than the reference light-emitting time. The determination result is output to the transmission-signal generator 131*b* and the light-emitting time attachment unit 133*b*.

Further, the light-emitting time 191 stored in the register 190 via the control unit 170 is input into the light-emitting time attachment unit 133*b*. When the image information is determined to be transmitted as a result of the determination by the transmission determination unit 135, the light-emitting time attachment unit 133*b* outputs the light-emitting time to the transmission-signal generator 131*b*. The transmission-signal generator 131*b* attaches the light-emitting time to the transmission signal.

Figure 11:
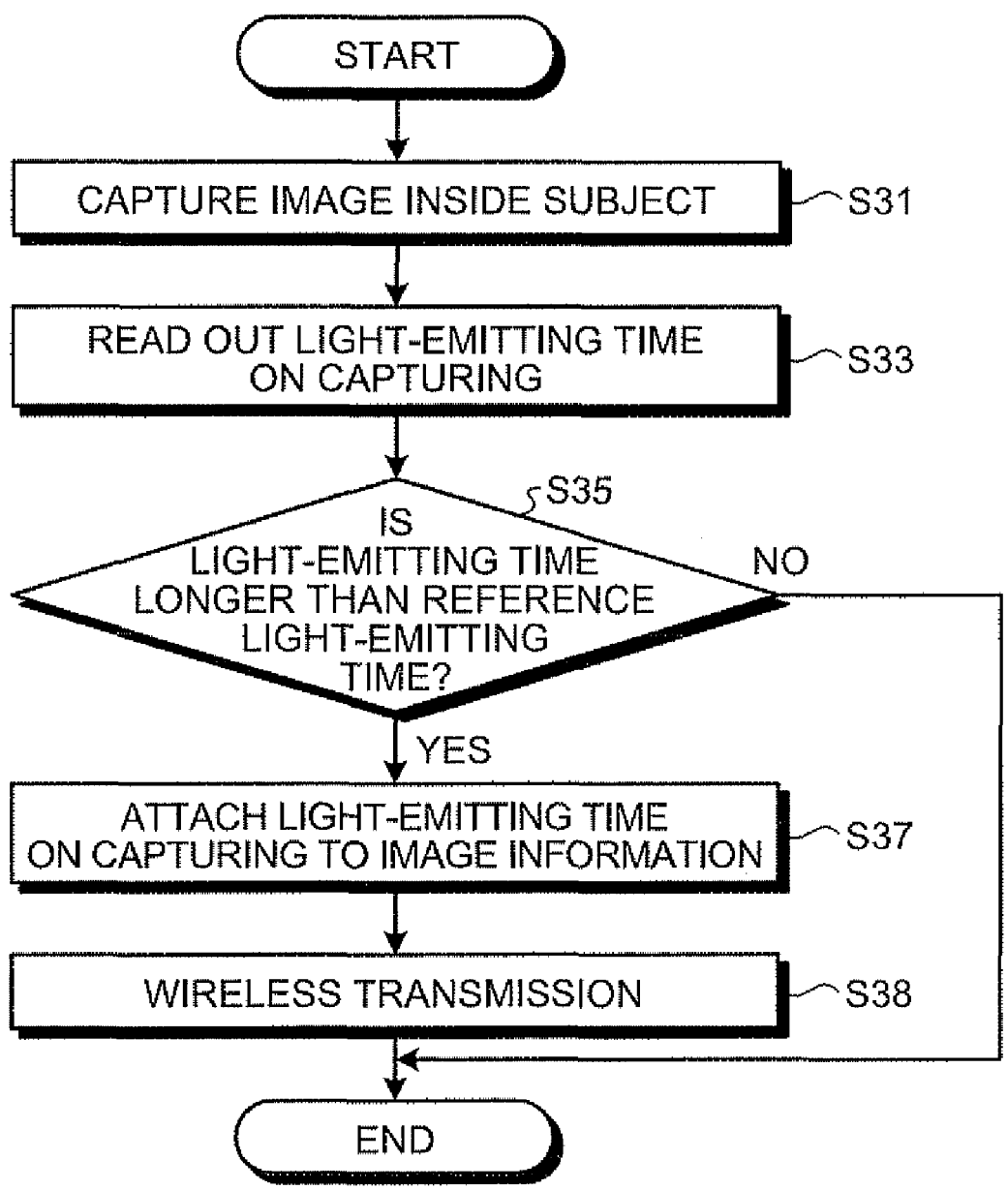
FIG. 11 is a process flowchart of the capsule endoscope according to the second embodiment.

An operational procedure of the capsule endoscope 10*b* according to the second embodiment is described below. FIG. 11 is an operational flowchart of the capsule endoscope 10*b* according to the transmission of the acquired image information. In the capsule endoscope 10*b*, firstly, the imaging unit 110 captures an inside of the subject 1 (Step S31). Next, the light-emitting time comparison unit 134 reads out the light-emitting time 191 stored in the register 190 via the control unit 170 (Step S33). The light-emitting time comparison unit 134 compares the light-emitting time of the illuminating unit 120 at the time of capturing to the reference light-emitting time. The transmission determination unit 135 determines, based on the comparison result, whether the image information is to be transmitted. Specifically, if the light-emitting time is longer than the reference light-emitting time (Step S35: Yes), the transmission signal generator 131*b* generates a transmission signal based on the acquired image information. On the other hand, the light-emitting time attachment unit 133*b* attaches the light-emitting time to the transmission signal to thereby attach the light-emitting time of the illuminating unit 120 at the time of capturing to the acquired image information (Step S38). On the other hand, if the light-emitting time is equal to or shorter than the reference light-emitting time (Step S35: No), the process is finished.

According to the second embodiment described above, the capsule endoscope 10*b* acquires the light-emitting time of the illuminating unit 120 at the time of capturing as information from which the distance between the head part of the front cover 13 and the wall surface of organ can be estimated. Further, the light-emitting time at the time of capturing is compared to the reference light-emitting time. Thus the acquired image information can be divided to those which are captured when the head part of the front cover 13 is close to the wall surface of organ, and those which are captured when the head part of the front cover 13 is away from the wall surface of organ. Based on the result of division, only the image information captured when the head part is close to the wall surface of organ can be transmitted to the outside of body. Therefore, the image information which needs to be checked for a screening test or the like can be automatically extracted, whereby the observer can shorten observation time, and avoid burden on visually dividing the image information. Further, since only images which need to be checked are transmitted, power consumption of the capsule endoscope 10b can be reduced.

Figure 12:
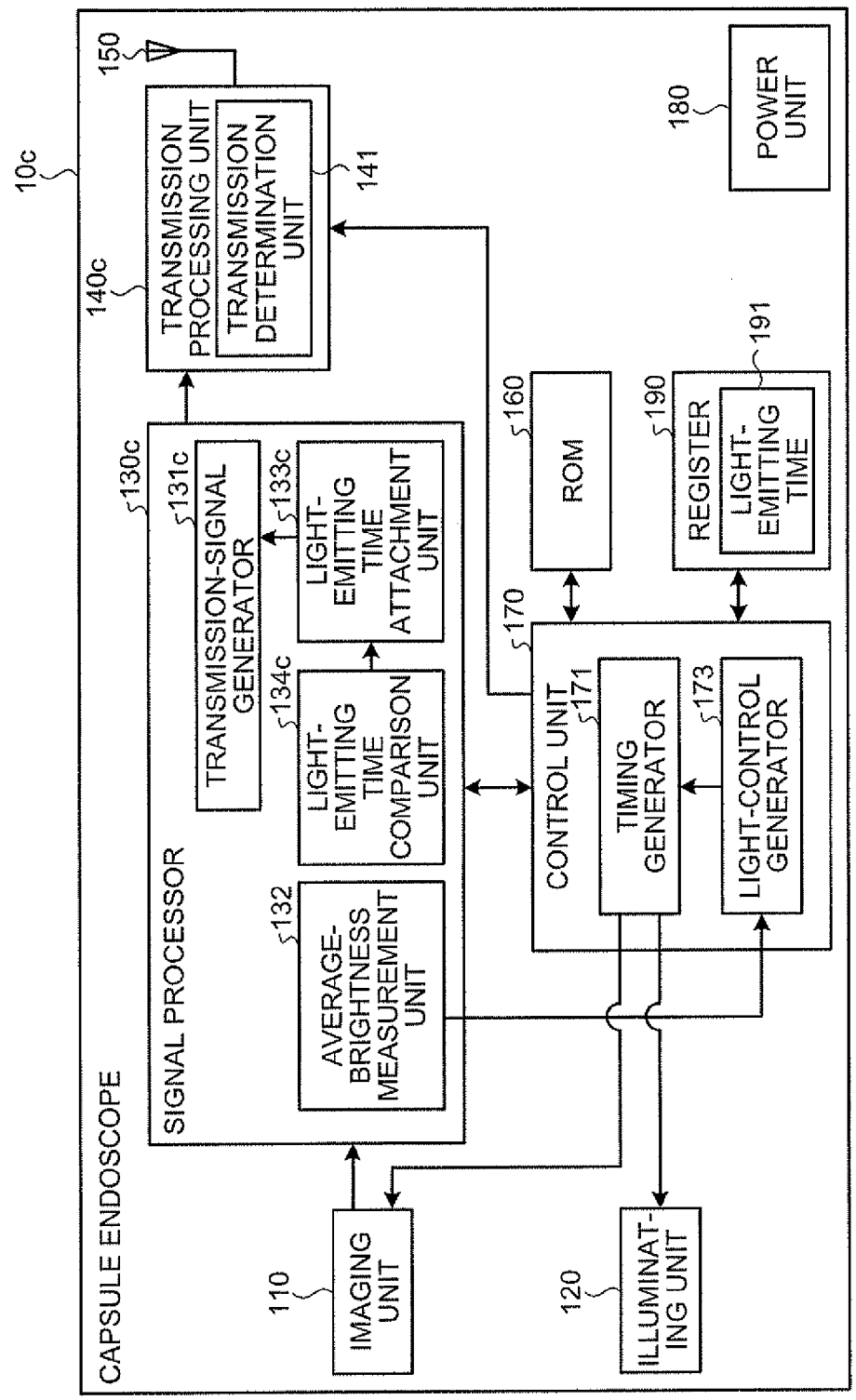
FIG. 12 is a block diagram explaining a functional configuration of a capsule endoscope according to a variation.

Further, in the second embodiment, the transmission determination unit 135 of the signal processor 130b determines whether the image acquired image information is to be transmitted, and generates, based on the result of determination, the transmission signal. Alternatively, the transmission signal 130b may generate the transmission signal regardless of the light-emitting time at the time of capturing and determine whether the transmission signal is to be transmitted. Further, the determination as to whether the image information is to be transmitted may be performed considering convergence time of the light-control control. FIG. 12 is a block diagram explaining a functional configuration of a capsule endoscope 10c according to the present variation. Same numerals are attached to components which are identical with the components of the second embodiment.

As shown in FIG. 12, the capsule endoscope 10c according to the present variation includes a signal processor 130 formed by a transmission-signal generator 131c, an average-brightness measurement unit 132, a light-emitting time comparison unit 134c, and a light-emitting time attachment unit 133c.

The transmission-signal generator 131c generates a transmission signal to wirelessly transmit the acquired image information to the outside of body, and attaches the light-emitting time information which is input from the light-emitting time attachment unit 133c to the generated signal. The transmission signal is output to the transmission processing unit 140c.

The light-emitting time 191 stored in the register 190 via the control unit 170 is input into the light-emitting time comparison unit 134c. The light-emitting time comparison unit 134c compares the input light-emitting time to the reference emitting time. The comparison result is output to the control unit 170. Further, the light-emitting time attachment unit 133c outputs the light-emitting time to the transmission-signal generator 131c, and attaches the light-emitting time to the transmission signal generated by the transmission-signal generator 131c.

Further, the transmission processing unit 140c includes a transmission determination unit 141. The transmission determination unit 141, under a control by the control unit 170, determines whether the transmission signal input from the transmission-signal generator 131c is to be transmitted. Then, the transmission processing unit 140c generates a wireless-transmission signal based on the transmission signal which is determined to be transmitted by the transmission determination unit 141, and performs a process to wirelessly transmit the generated wireless-transmission signal to an outside via a transmission antenna 150.

Further, in the present variation, the control unit 170 controls the operation of the transmission determination unit 141 based on the comparison result input from the light-emitting time comparison unit 134c. Specifically, the control unit 170 controls the transmission determination unit 141 to determine that the transmission signal input from the transmission-signal generator 131c is to be transmitted when the light-emitting time of the illuminating unit 120 at the time of capturing is longer than the reference light-emitting time as the result of comparison by the light-emitting time comparison unit 134c. On the other hand, the control unit 170 controls the transmission determination unit 141 to determine that the transmission signal input from the transmission-signal generator 131c is not to be transmitted when the light-emitting time of the illuminating unit 120 at the time of capturing is equal to or shorter than the reference light-emitting time.

Figure 13:
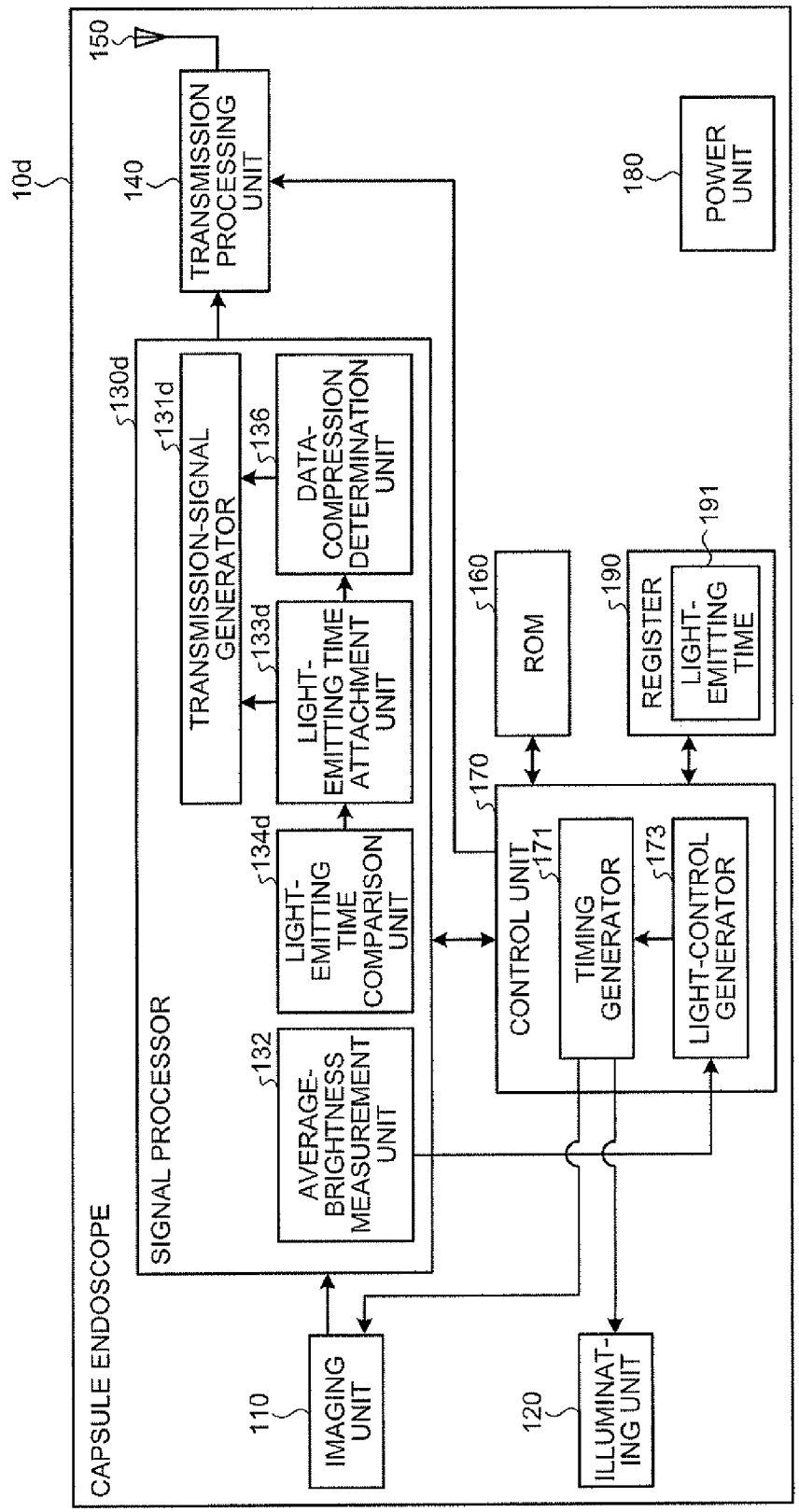
FIG. 13 is a block diagram explaining a functional configuration of a capsule endoscope according to a third embodiment.

Next, a third embodiment is described below. FIG. 13 is a block diagram of a functional configuration of a capsule endoscope 10d according to the third embodiment. Same numerals are attached to components which are identical with the components of the first embodiment.

As shown in FIG. 13, the capsule endoscope 10d includes a signal processor 130d formed by a transmission-signal generator 131d, an average-brightness measurement unit 132, a light-emitting time comparison unit 134d, a light-emitting time attachment unit 133d, a data-compression determination unit 136.

The transmission-signal generator 131d generates a transmission signal to wirelessly transmit the acquired image information to the outside of body, and attaches the light-emitting time information input from the light-emitting time attachment unit 133d to the generated transmission signal. Further, when the image information is determined to be compressed by the data-compression determination unit 136 as described later, the transmission-signal generator 131d performs a compression process on the image information. For the encoding, an irreversible compression such as JPEG is adopted for example. Alternatively, a reversible method may be adopted. The transmission signal is output to the transmission processing unit 140.

The light-emitting time 191 stored in the register 190 via the control unit 170 is input into the light-emitting time comparison unit 134d. The light-emitting time comparison unit 134d compares the input light-emitting time to the reference light-emitting time. Further, the light-emitting time attachment unit 133d outputs the light-emitting time to the transmission-signal generator 131d so as to attach the light-emitting time to the transmission signal generated by the transmission-signal generator 131d.

The data-compression determination unit 136 determines whether the image information is to be compressed based on the comparison result by the light-emitting time comparison unit 134d. Specifically, the data-compression determination unit 136 determines that the image information is not to be compressed when the light-emitting time of the illuminating unit 120 at the time of capturing is longer than the reference light-emitting time as the result of comparison by the light-emitting time comparison unit 134d. On the other hand, the data-compression determination unit 136 determines that the image information is to be compressed when the light-emitting time of the illuminating unit 120 at the time of capturing is equal to or shorter than the reference light-emitting time. The result of determination is output to the transmission-signal generator 131d.

Figure 14:
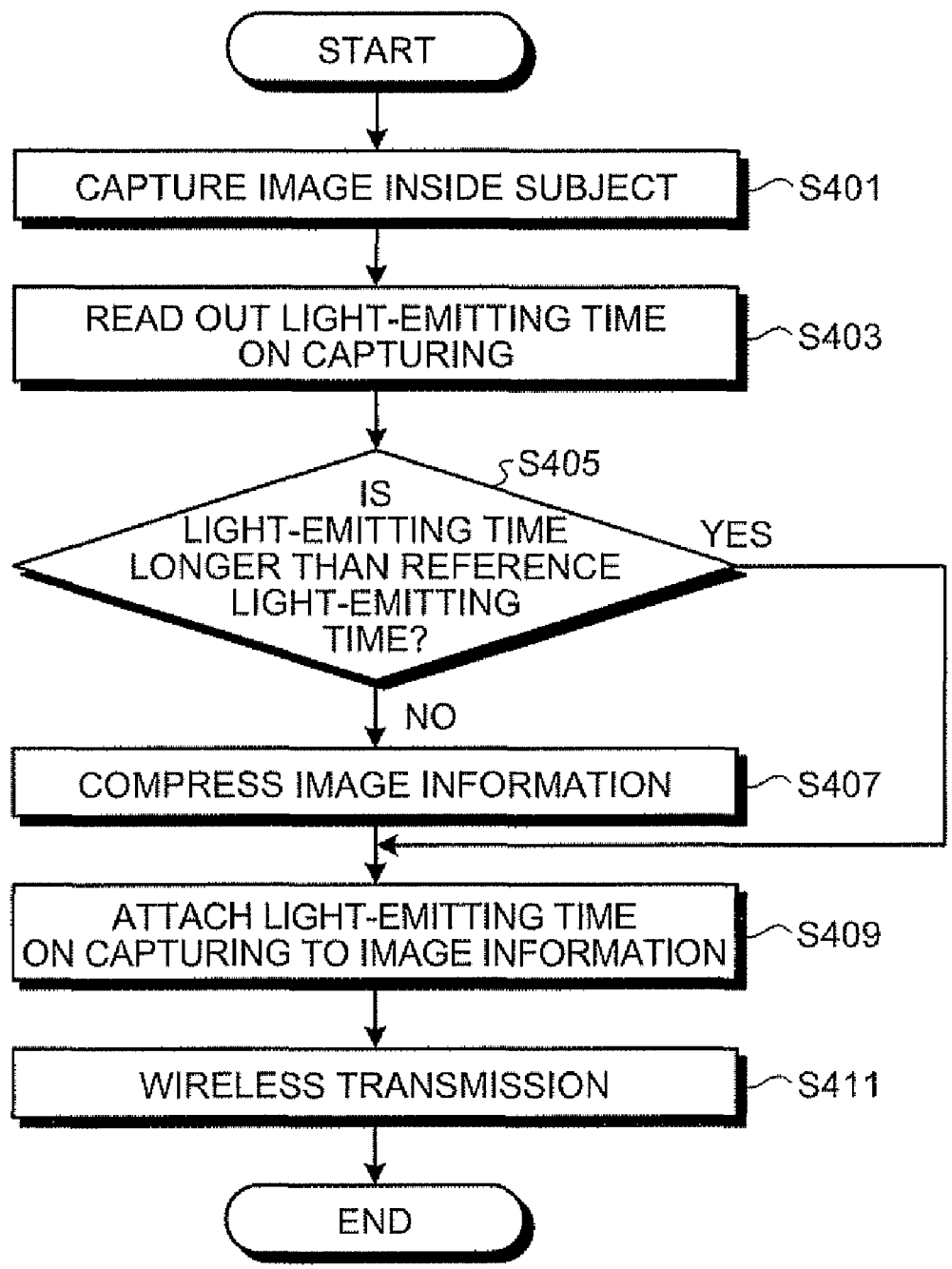
FIG. 14 is a process flowchart of the capsule endoscope according to the third embodiment.

Next, an operational procedure of the capsule endoscope 10d according to the third embodiment is described below. FIG. 14 is an operational flowchart of the capsule endoscope 10d according to the transmission of the acquired image information. In the capsule endoscope 10d, firstly, the imaging unit 110 captures an inside of the subject 1 (Step S401). Next, the transmission-signal generator 131d generates a transmission signal based on the image information acquired by the imaging unit 110 while the light-emitting time comparison unit 134d reads out the light-emitting time 191 stored in the register 190 via the control unit 170 (Step S403). The light-emitting time comparison unit 134*d* compares the light-emitting time of the illuminating unit 120 at the time of capturing to the reference light-emitting time. The data-compression determination unit 136 determines, based on the result of comparison, whether the image information is to be compressed. Specifically, if the light-emitting time is longer than the reference light-emitting time (Step S405: Yes), the control unit 170 proceeds to Step S409. On the other hand, if the light-emitting time is equal to or shorter than the reference light-emitting time (Step S405: No), the data-compression determination unit determines that the image information is to be compressed, and outputs the result of determination to the transmission-signal generator 131*d*. Based on the result of determination, the transmission-signal generator 131*d* compresses the image information (Step S407). Further, the light-emitting time attachment unit 133*d* attaches the light-emitting time to the transmission signal to thereby attach the light-emitting time of the illuminating unit 120 to the acquired image information (Step S409). Then, the transmission processing unit 140 performs a process to wirelessly transmit the transmission signal input from the transmission-signal generator 131*d* to the outside of body (Step S411).

According to the third embodiment described above, the capsule endoscope 10*d* can acquire the light-emitting time of the illuminating unit 120 at the time of capturing as information from which the distance between the head part of the front cover 13 and the wall surface of organ can be estimated. Further, the capsule endoscope 10*d* compares the light-emitting time at the time of capturing to the reference light-emitting time. Thus, the acquired image information can be divided to those which are captured when the head part of the front cover 13 is close to the wall surface of organ, and those which are captured when the head part of the front cover 13 is away from the wall surface of organ. Based on the result of division, only the image information captured when the head part is close to the wall surface of organ can be compressed. Since the irreversible compression method is adopted for the encoding, the image information on which the compression process has been performed deteriorates after the encoding, meanwhile a compression rate higher than that of the reversible encoding can be achieved. Therefore, the operation time of the transmission processing unit 140 according to the transmission of the image information can be shortened and power consumption can be reduced.

In the third embodiment, the determination as to whether the image information is to be compressed is performed based on the light-emitting time at the time of capturing. Further, curtailing operation or a clipping operation may be performed on the image information whose light-emitting time at the time of capturing is equal to or shorter than the reference light-emitting time. Further, the determination as to whether the compression is to be performed or whether the curtailing operation or the clipping operation to be performed may be performed considering the convergence time of the light-control control.

Figure 15:
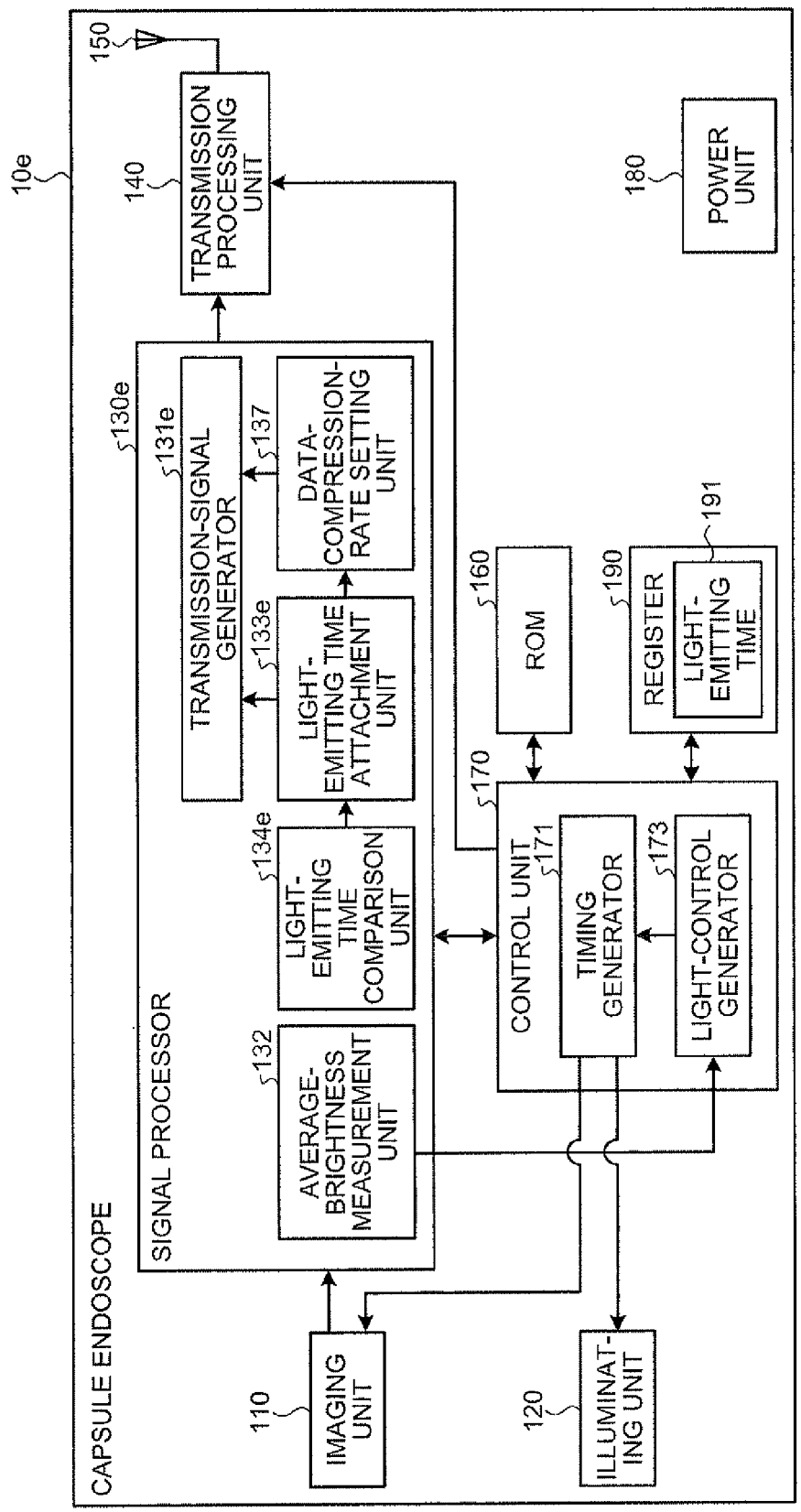
FIG. 15 is a block diagram explaining a functional configuration of a capsule endoscope according to a fourth embodiment.

Next, a fourth embodiment is described. FIG. 15 is a block diagram explaining a functional configuration of a capsule endoscope 10*e* according to the fourth embodiment. Same numerals are attached to components which are identical with the components of the first embodiment.

As shown in FIG. 15, the capsule endoscope 10*e* includes a signal processor 130*e* formed by a transmission-signal generator 131*e*, an average-brightness measurement unit 132, a light-emitting time comparison unit 134*e*, a light-emitting time attachment unit 133*e*, a data-compression-rate setting unit 137.

The transmission-signal generator 131*e* generates a transmission signal to wirelessly transmit the acquired image information to the outside of body, and attaches the light-emitting time information input from the light-emitting time attachment unit 133*e* to the generated transmission signal. Further, the transmission-signal generator 131*e* performs a compression process on the image information according to the compression rate set by the data-compression-rage setting unit 137 as described later.

The data-compression-rate setting unit 137 sets a compression rate based on the result of comparison by the light-emitting time comparison unit 134*e*. Specifically, the data-compression-rate setting unit 137 sets the compression rate at a predetermined value X and outputs the same to the transmission-signal generator 131*e* when the light-emitting time of the illuminating unit 120 at the time of capturing is longer than the reference light-emitting time as the result of comparison by the light-emitting time comparison unit 134*e*. On the other hand, the data-compression-rate setting unit 137 sets the compression rate at a predetermined value Y (>X) and outputs the same to the transmission-signal generator 131*e* when the light-emitting time of the illuminating unit 120 at the time of capturing is equal to or shorter than the reference light-emitting time.

Figure 16:
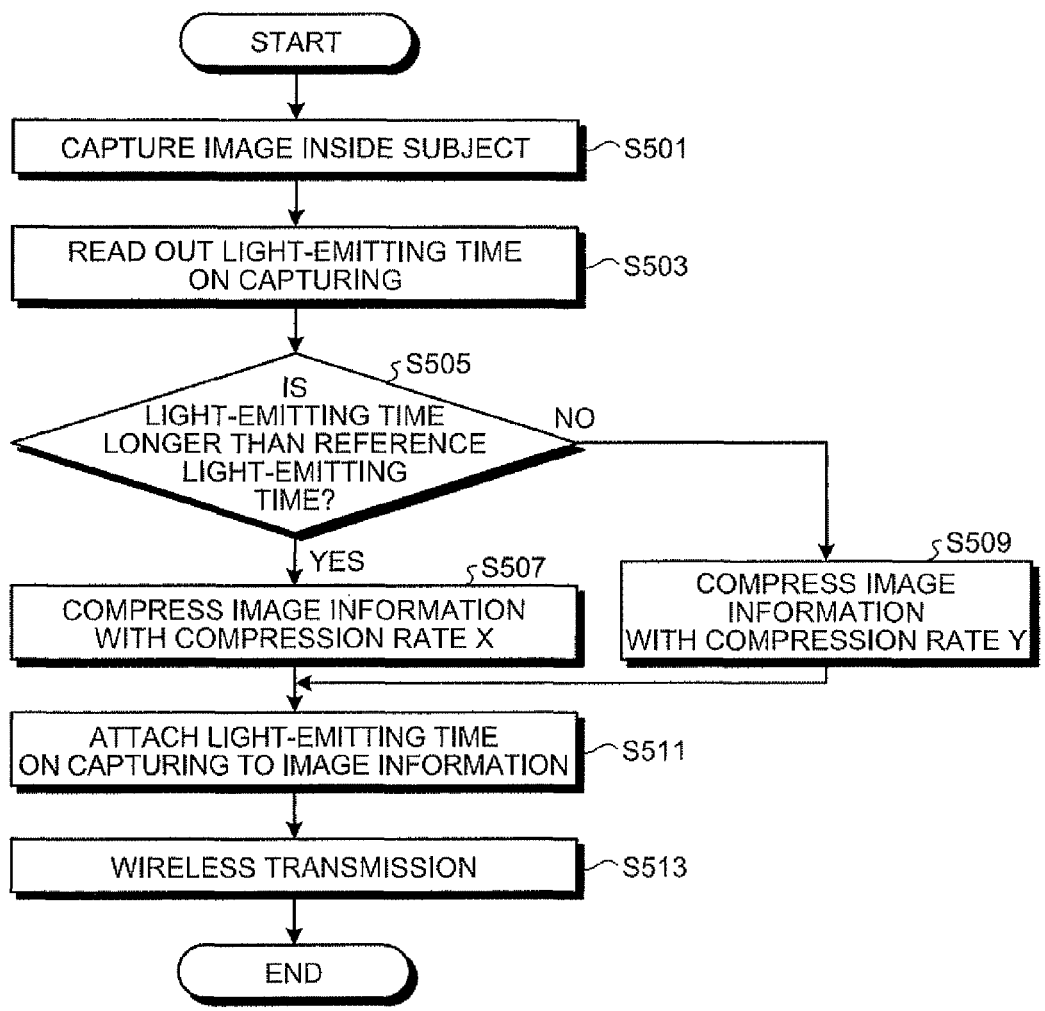
FIG. 16 is a process flowchart of the capsule endoscope according to the fourth embodiment.

An operational procedure of the capsule endoscope 10*e* according to the fourth embodiment is described below. FIG. 16 is an operational flowchart of the capsule endoscope 10*d* according to the transmission of the acquired image information. In the capsule endoscope 10*d*, firstly, the imaging unit 110 captures the inside of subject 1 (Step S501). Then, the transmission-signal generator 131*e* generates the transmission signal based on the image information acquired by the imaging unit 110 while the light-emitting time comparison unit 134*e* reads out the light-emitting time 191 from the register 190 via the control unit 170 (Step S503). Further, the light-emitting time comparison unit 134*e* compares the light-emitting time of the illuminating unit 120 at the time of capturing to the reference light-emitting time, and the data-compression-rate setting unit 137 sets the compression rate of the image information based on the result of comparison. Specifically, if the light-emitting time is longer than the reference light-emitting time (Step S505: Yes), the data-compression-rate setting unit 137 outputs the compression rate X to the transmission-signal generator 131*e*. Accordingly, the transmission-signal generator 131*e* compresses the image information by the compression rate X (Step S507). On the other hand, the light-emitting time is equal to or shorter than the reference light-emitting time (Step S505: Yes), the data-compression-rate setting unit 137 outputs the compression rate Y to the transmission-signal generator 131*e*. Accordingly, the transmission-signal generator 131*e* compresses the image information by the compression rate Y (>X) (Step S509). Further, the light-emitting time attachment unit 133*e* attaches the light-emitting time to the transmission signal to thereby attach the light-emitting time of the illuminating unit 120 at the time of capturing to the acquired image information (Step S511). The transmission unit 140 performs a process to wirelessly transmit the transmission signal input from the transmission-signal generator 131*e* to the outside of body (Step S513).

According to the fourth embodiment described above, the capsule endoscope 10*e* can acquire the light-emitting time of the illuminating unit 120 at the time of capturing as information from which distance between the head part of the front cover 13 and the wall surface of organ can be estimated. Further, the capsule endoscope 10*d* compares the light-emitting time at the time of capturing to the reference light-emitting time so that the acquired image information can be divided into those which are captured when the head part of the front cover 13 is close to the wall surface of organ, and those which are captured when the head part of the front cover 13 is away from the wall surface of organ. Based on the result of division, only the image information captured when the head part is close to the wall surface of organ can be compressed by the higher compression rate that the rate for the image information captured when the head part is away from the wall surface of organ. Therefore, the operation time of the transmission processing unit 140 according to the transmission of the image information which is not suitable for observation can be saved, and power consumption can be reduced.

Further, in the fourth embodiment, the compression process is performed on the acquired image information, and the compression rate for the compression is set based on the light-emitting time at the time of capturing. Further, the curtailing process may be performed on the acquired image information. Further, the curtailment rate for curtailing may be set based on the light-emitting time at the time of capturing.

Figure 17:
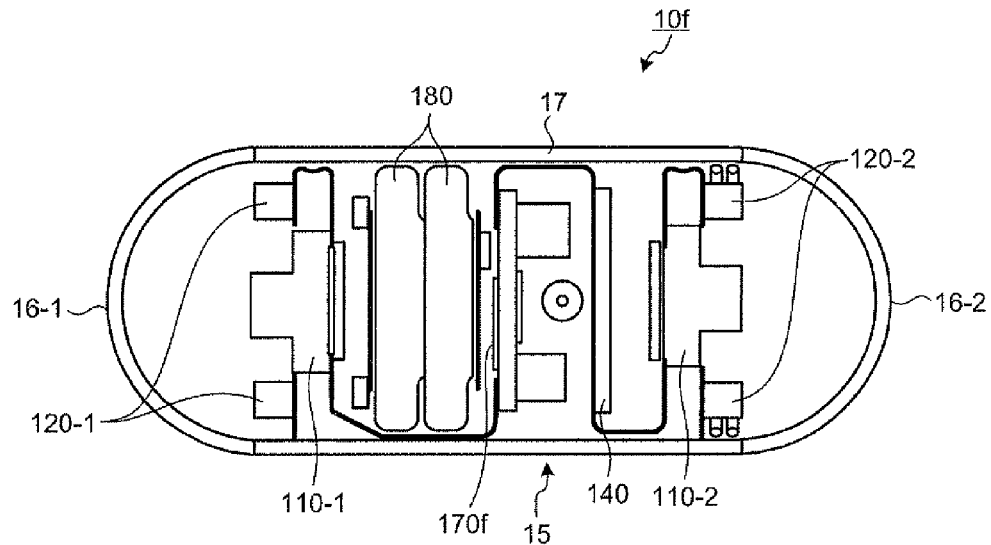
FIG. 17 is a schematic diagram of a configuration of the capsule endoscope according to the variation.
Figure 18:
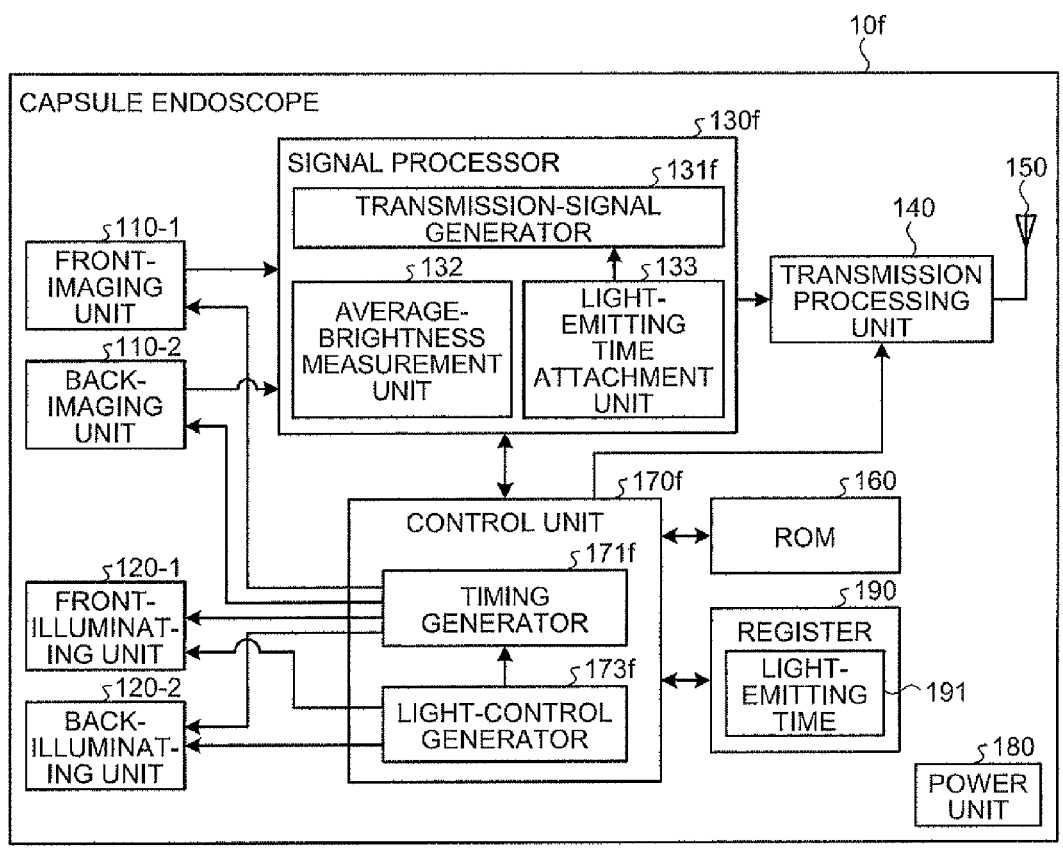
FIG. 18 is a block diagram of a functional configuration of the capsule endoscope according to a variation.

Further, in the embodiments from first to fourth described above, the capsule endoscope is described to have the configuration including a pair of the imaging unit and the illuminating unit. Further, the capsule endoscope having a configuration including two or more pairs of the imaging unit and the illuminating unit may be applied similarly. FIG. 17 is a schematic configuration diagram of a capsule endoscope 10$f$ including two pairs of the imaging unit and the illuminating unit. FIG. 18 is a block diagram of a functional configuration of the capsule endoscope 10$f$. Same numerals are attached to components which are identical with the components of the first embodiment.

The capsule endoscope 10$f$ employs the imaging unit and the illuminating unit on both head parts thereof so that the capsule endoscope 131$f$ can capture the image information both in front and in back inside the subject 1. Specifically, as shown in FIGS. 17 and 18, the capsule endoscope 10$f$ contains inside a capsule container 15 a front-imaging unit 110-1 and a back-imaging unit 110-2, a front-illuminating unit 120-1 and a back-illuminating unit 120-2, a signal processor 130$f$, a transmission processing unit 140, a transmission antenna 150, a ROM 160, a register 190, a control unit 170$f$, a power unit 180, and the like.

The container 15 is formed with substantially hemispherical front covers 16-1, 16-2, and a cylindrical body cover 17 forming a joint. The front covers 16-1, 16-2 are made of a transparent material, and work as optical windows. Specifically, the front cover 16-1 allows illuminating light from the front-illuminating unit 120-1, which is arranged at an opposing position to the front cover 16-1 inside the container 15, to transmit through the front cover 16-1 to an outside of the container 15, and introduces reflected light thereof to an inside of the container 15. Similarly, the front cover 16-2 allows illuminating light from the back-illuminating unit 120-2, which is arranged at an opposing position to the front cover 16-1 inside the container 15, to transmit through the front cover 16-1 to an outside of the container 15, and introduces reflected light thereof to an inside of the container 15. The front-imaging unit 110-1 and the back-imaging unit 110-2 perform, under a control by a timing generator 171$f$, imaging operations at the same timing. Further, the front-imaging unit 110-1 and the back-imaging unit 110-2 perform, under a control by the timing generator 171$f$, illuminating operations at the same timing. A light-control unit 173$f$ determines a light-control amount based on brightness of the image information acquired last time by the imaging units 110-1, 110-2, and performs a light-control control of the illuminating units 120-1, 120-2.

In the signal processor 130$f$ of the capsule endoscope 10$f$, the transmission-signal generator 131$f$ generates a transmission signal to wirelessly transmit the acquired image information to the outside of body. The transmission-signal generator 131$f$ attaches imaging-unit-identification information indicating which has captured the acquired image information, an imaging operation of the imaging unit 110-1 or 110-2, to the acquired image information. Further, similarly to the first embodiment, the transmission-signal generator 131$f$ attaches the information of light-emitting time and attached information which are input from the light-emitting time attachment unit 133 to the acquired image information, to thereby generate the transmission signal. The generated transmission signal is transmitted by the transmission processing unit 140 to the receiving apparatus 30 arranged outside the body.

Figure 19:
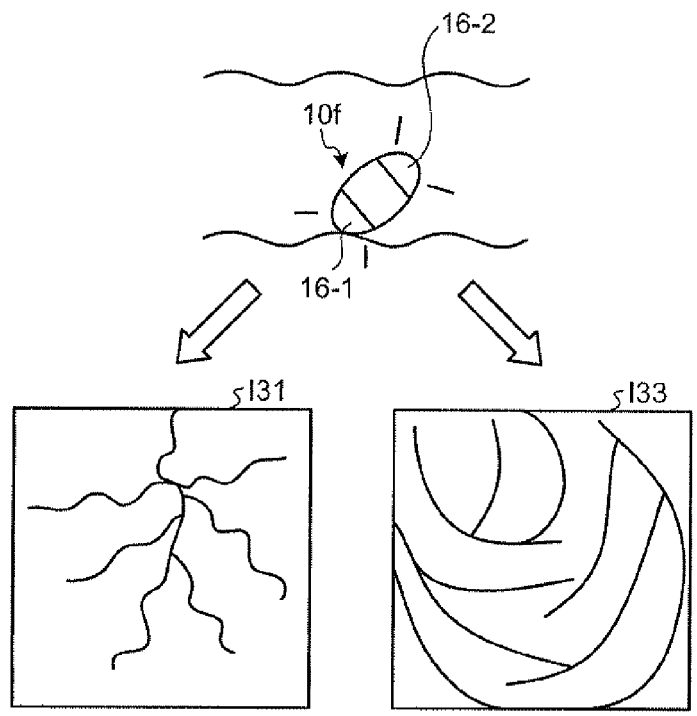
FIG. 19 is an explanatory diagram showing an example state of the capsule endoscope, and an example of an acquired image according to a variation.

FIG. 19 is an explanatory diagram showing an example state of the capsule endoscope 10$f$ and an example of acquired image when the capsule endoscope 10$f$ is in the cavity of large intestine. In the example shown in FIG. 19, the capsule endoscope 10$f$ is in a state where the front cover 16-1 is close to the intestine wall and others while the front cover 16-2 faces in a direction to the cavity side. Thus, an image 131 captured by the front-imaging unit 110-1 on a side of the front cover 16-1 covers only a small limited area of the intestine wall. On the other hand, an image I33 captured by the back-imaging unit 110-2 on a side of the front cover 16-2 broadly covers an overview of the cavity. Thus, the image I33 is useful.

The receiving apparatus 30 which receives the image information wirelessly transmitted from the capsule endoscope 10$f$ and the display apparatus 70 perform, for example, a process to display on screen, side-by-side, information of two images captured by the front-imaging unit 110-1 and the back-imaging unit 110-2 of the capsule endoscope 10$f$ at the same timing. Then, for example, the light-emitting time at the time of capturing is compared to the reference light-emitting time. When the light-emitting time at the time of capturing is longer than the reference light-emitting time in one of the image information as the result of comparison, the image information at the time of capturing, i.e., when it is determined that one of the image information is captured at a position away from the wall surface of organ (e.g., a case shown in FIG. 19), the information of the image and that of another image are displayed on screen side-by-side. Alternatively, both of the image information may be displayed on screen side-by-side only when the light-emitting time at the time of capturing is longer than the reference light-emitting time in both of the image information, i.e., when it is determined that both of the image information are captured at a position away from the wall surface of organ. In this case, when the light-emitting time at the time of capturing is equal to or shorter than the reference light-emitting time in one of the image information, both of pieces of the image information are not displayed.

Further, similarly to the second embodiment, it may be determined, based on the light-emitting time at the time of capturing, whether the image information acquired by the front-imaging unit 110-1 and the back-imaging unit 110-2 is to be transmitted. For example, when the light-emitting time in both of the image information at the time of capturing is longer than reference light-emitting time as the result of comparison between the light-emitting time at the time of capturing and the reference light-emitting time, both of the image information may be transmitted. Alternatively, both of the image information may be transmitted when the light-emitting time in one of the image information at the time of capturing is longer than the reference light-emitting time. Further, similarly to the third embodiment, it may be determined, based on the light-emitting time at the time of capturing, whether the image information acquired by the front-imaging unit 110-1 and the back-imaging unit 110-2 is to be compressed, respectively. Alternatively, similarly to the fourth embodiment, a compression rate may be determined, based on the light-emitting time at the time of capturing, for the image information acquired by the front-imaging unit 110-1 and the back-imaging unit 110-2, respectively.

Further, from the second embodiment to the fourth embodiment, the capsule endoscope attaches the light-emitting time information to the image information and wirelessly transmits the image information to the receiving apparatus 30. Alternatively, the capsule endoscope may wirelessly transmit the image information without attaching the light-emitting time information to the image information.

Further, from the first embodiment to the fourth embodiment, the light-emitting time at the time of capturing is compared to the reference light-emitting time. Then, the acquired image information is divided to those which are captured when the head part on the side of front cover of the capsule endoscope is close to the wall surface of organ, and those which are captured when the head part is away from the wall surface of organ. Besides, the image information may be divided to more groups, for example, by setting plural reference light-emitting times in stages. For example, by setting the reference light-emitting time in two stages, the image information can be divided to three groups based on the light-emitting time at the time of capturing. First group is the image information determined as being captured when the front cover is in close contact with the wall surface of organ because the head part on the side of front cover of the capsule endoscope is close to the wall surface of organ. Second one is the image information determined as being captured when the front cover is in a direction to the cavity because the head part on the side of front cover of the capsule endoscope is away from the wall surface of organ, i.e. Third one is the image information determined as being captured when the capsule endoscope faces in an oblique direction to the cavity because the head part on the side of front cover of the capsule endoscope is in middle distance from the wall surface of organ. Further, in this case, the compression rate for the compression of the image information can be suitably adjusted depending on the group of the image information.

Figure 20A:
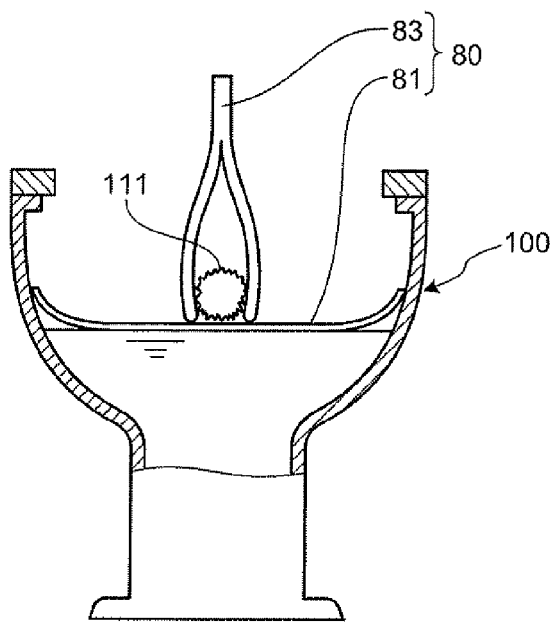
FIG. 20A is an explanatory diagram of a retriever for a capsule endoscope and a retrieval method thereof according to a fifth embodiment.
Figure 20B:
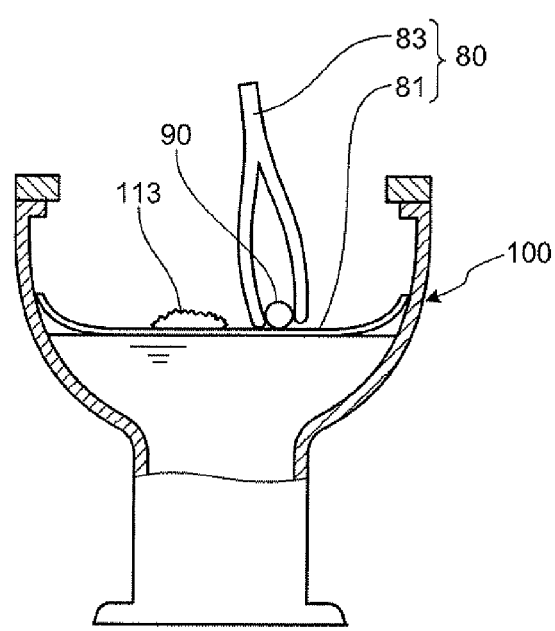
FIG. 20B is an explanatory diagram of the retriever for the capsule endoscope and the retrieval method thereof according to the fifth embodiment.

Next, a fifth embodiment is described. FIGS. 20A and 20B are diagrams explaining a retriever 80 of a capsule medical apparatus according to the fifth embodiment and retrieval method therefor, and showing states inside the toilet bowl 100 as cross sections, respectively. The retriever 80 according to the fifth embodiment is used for retrieving the capsule medical apparatus which is discharged outside the body along with stool. As shown in FIG. 20A and others, the retriever 80 includes a water-soluble sheet 81 and a gripping member 83.

Figure 21:
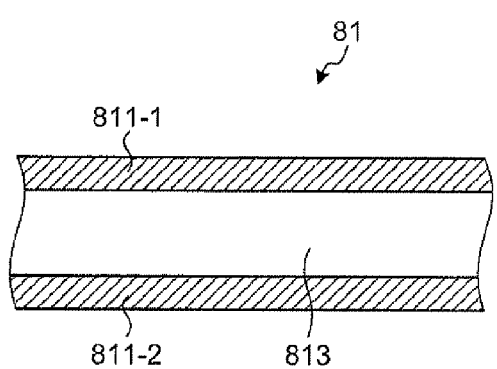
FIG. 21 is a cross-sectional view showing schematically an internal configuration of a water-soluble sheet.

Water is filled inside the toilet bowl 100 up to the predetermined water level at all times. The water-soluble sheet 81 is arranged on the water-surface of reserved water in the toilet bowl 100. FIG. 21 is a cross-sectional view showing schematically an internal configuration of the water-soluble sheet 81. As shown in FIG. 21, the water-soluble sheet 81 has, for example, a double-layer structure where the two water-soluble sheets 811-1, 811-2 are stacked, and an air layer 813 is formed between each of the water-soluble sheets 811-1, 811-2. Accordingly, the water-soluble sheet 81 is more likely to float on the water surface of reserved water in the toilet bowl 100, whereby the retrieval of the capsule medical apparatus can be accurately performed. More specifically, the water-soluble sheet 81 is made large enough to cover the entire wall surface of reserved water in the toilet bowl 100. Alternatively, instead of the water-soluble sheet 81, a single-layer structure may be adopted. Still alternatively, a multiple-layer structure where three or more water-soluble sheets are stacked and the air layer is formed between each of the water-soluble sheet may be adopted.

Figure 22:
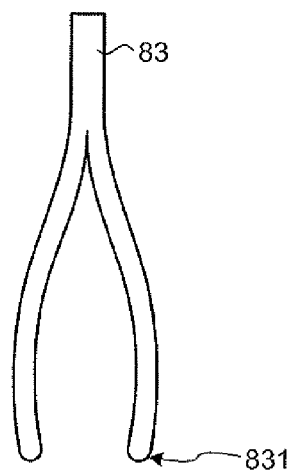
FIG. 22 is a plan view of a gripping member.

The gripping member 83 is used for gripping the capsule medical apparatus discharged onto the water-soluble sheet 81 along with stool, and is realized, for example, by tweezers. FIG. 22 is a plan view of the gripping member 83. As shown in FIG. 22, the head part 831 of the gripping member 83 has a cross section forming a curved surface so that the water-soluble sheet 81 is not likely to be torn. Preferably, a non-skid treatment is performed on the head part 831 of the gripping member 83 so that the capsule medical apparatus can be easily gripped. Further, the gripping member 83 is disposed after use. Therefore, it is preferable that the gripping member 83 is made of cheap plastic or a paper to be disposed after use.

Next, the method for retrieving the capsule medical apparatus with the retriever 80 is described. In advance for retrieving the capsule medical apparatus, firstly, the water-soluble sheet 81 is arranged on the water surface of reserved water in the toilet bowl 100. After a bowl movement, as shown in FIG. 20A, the stool 111 discharged onto the water-soluble sheet 81 is broken using the gripping member 83 without tearing the water-soluble sheet 81, and the capsule medical apparatus is searched. Specifically, the gripping member 83 sandwiches the stool from sides so that no force is caused in a direction substantially vertical to the water-surface of reserved water in the toilet bowl 100, and the stool is broken by gripping force acting in a direction substantially horizontal to the water-surface of reserved water in the toilet bowl 100, whereby the capsule medical apparatus is searched. Then, as shown in FIG. 20B, the capsule medical apparatus 90 found from the broken stool 113 is gripped and retrieved by the gripping member 83. After the capsule medical apparatus 90 is retrieved, the water-soluble sheet 81 is discharged with the reserved water in the toilet bowl 100.

Figure 23:
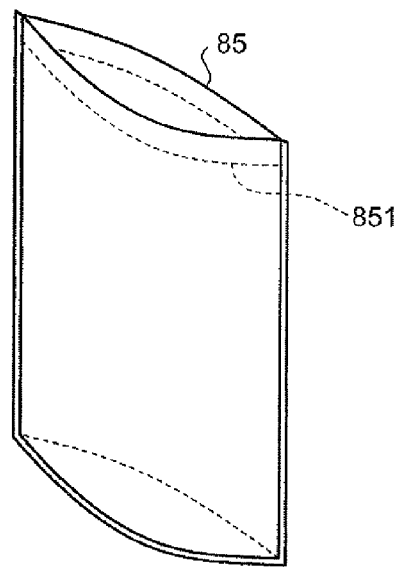
FIG. 23 is a diagram of an example of a storage bag.

The retrieved capsule medical apparatus 90 and the gripping member 83 are stored in a storage bag, and disposed as the storage bag. Alternatively, a hospital or a manufacturer of the capsule medical apparatus may collect the retrieved capsule medical apparatus 90 and the gripping member 83. FIG. 23 is a diagram showing an example of the storage bag 85. The storage bag 85 is a bag for storing the capsule medical apparatus 90 and the gripping member 83 which has gripped and retrieved the capsule medical apparatus 90. The storage bag 85 is made, for example, of nylon-laminated or polyethylene-laminated material, and is made opaque with aluminum deposited thereon like an aluminum-laminated zip-top bag. Further, a zip 851 is formed on an upper opening of the storage bag 85 so that the capsule medical apparatus 90 and the gripping member 83 can be sealed and stored in the storage bag 85. According to the storage bag 85, a development of bad odor is prevented and the waste materials are kept obscure. Further, plural storage bags may be prepared so that another storage bag can further store the storage bag, for example, in case an outer surface of the storage bag is tainted by the stool. Further, the capsule medical apparatus 90 and the gripping member 83 may be separately stored in the storage bags and disposed.

According to the fifth embodiment described above, since the stool is caught by the water-soluble sheet 81 arranged on the water surface of reserved water in the toilet bowl 100, the capsule medical apparatus 90 discharged onto the water-soluble sheet along with the stool can be searched and retrieved. Conventionally, when the capsule medical apparatus is retrieved in a Western-style toilet, a long rod-shaped retriever which can touch a bottom of the toilet bowl is needed for retrieving the capsule medical apparatus 90 from the stool. According to the fifth embodiment, however, the capsule medical apparatus 90 can be searched as the stool is broken on the water-soluble sheet 81, whereby the retriever is no longer necessary to be made long. Further, since the stool is caught by the water-soluble sheet 81, the water-soluble sheet 81 can be discharged along with the reserved water in the toilet bowl 100 after the capsule medical apparatus 90 is retrieved.

Further, since the stool is caught by the water-soluble sheet 81 arranged on the water-surface of reserved water in the toilet bowl 100, the water-soluble sheet 81 is likely to be torn or to sink down. According to the fifth embodiment, the gripping member 83 realized by tweezers sandwiches and grips the stool so that the stool on the water-soluble sheet 81 can be broken with no force acting on the water-soluble sheet 81, and the found capsule medical apparatus 90 can be gripped. Thus, the water-soluble sheet 81 is unlikely to be torn up and to sink down when the capsule medical apparatus 90 is retrieved, whereby the retrieval operation for the capsule medical apparatus 90 can be easily performed. Further, the head part of the gripping member 83 forms a curved surface, whereby the water-soluble sheet 81 is further unlikely to be torn up when the stool is broken on the water-soluble sheet 81 and the capsule medical apparatus 90 is searched.

Further, a water-repellent treatment or a water-sprinkling treatment may be performed, at least, on a surface of the water-soluble sheet 81 which faces the water surface when the water-soluble sheet 81 is arranged on the surface of reserved water in the toilet bowl 100. Accordingly, time for the water-soluble sheet 81 to dissolve in the reserved water inside the toilet bowl 100 can be controlled, whereby the retrieval operation can be performed even more easily.

Figure 24:
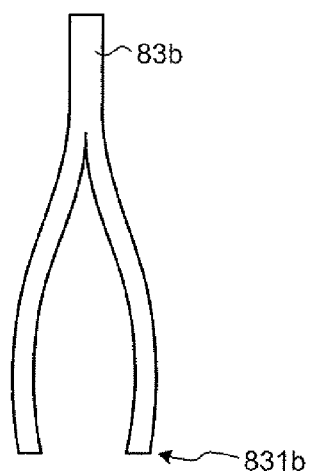
FIG. 24 is a plan view of a gripping member according to a variation.

Further, the shape of the head part of gripping member is not limited the description above. FIG. 24 is a plan view of a gripping member 83b according to the present variation. In the example shown in FIG. 24, the head part 831b of the gripping member 83b is formed flat so that the head part 831 is substantially parallel to a sheet surface of the water-soluble sheet when the stool is broken on the water-soluble sheet, and the capsule medical apparatus is gripped. Thus, the stool on the water-soluble sheet can be broken with no force acting on the water-soluble sheet, and the found capsule medical apparatus can be gripped and retrieved.

Figure 25:
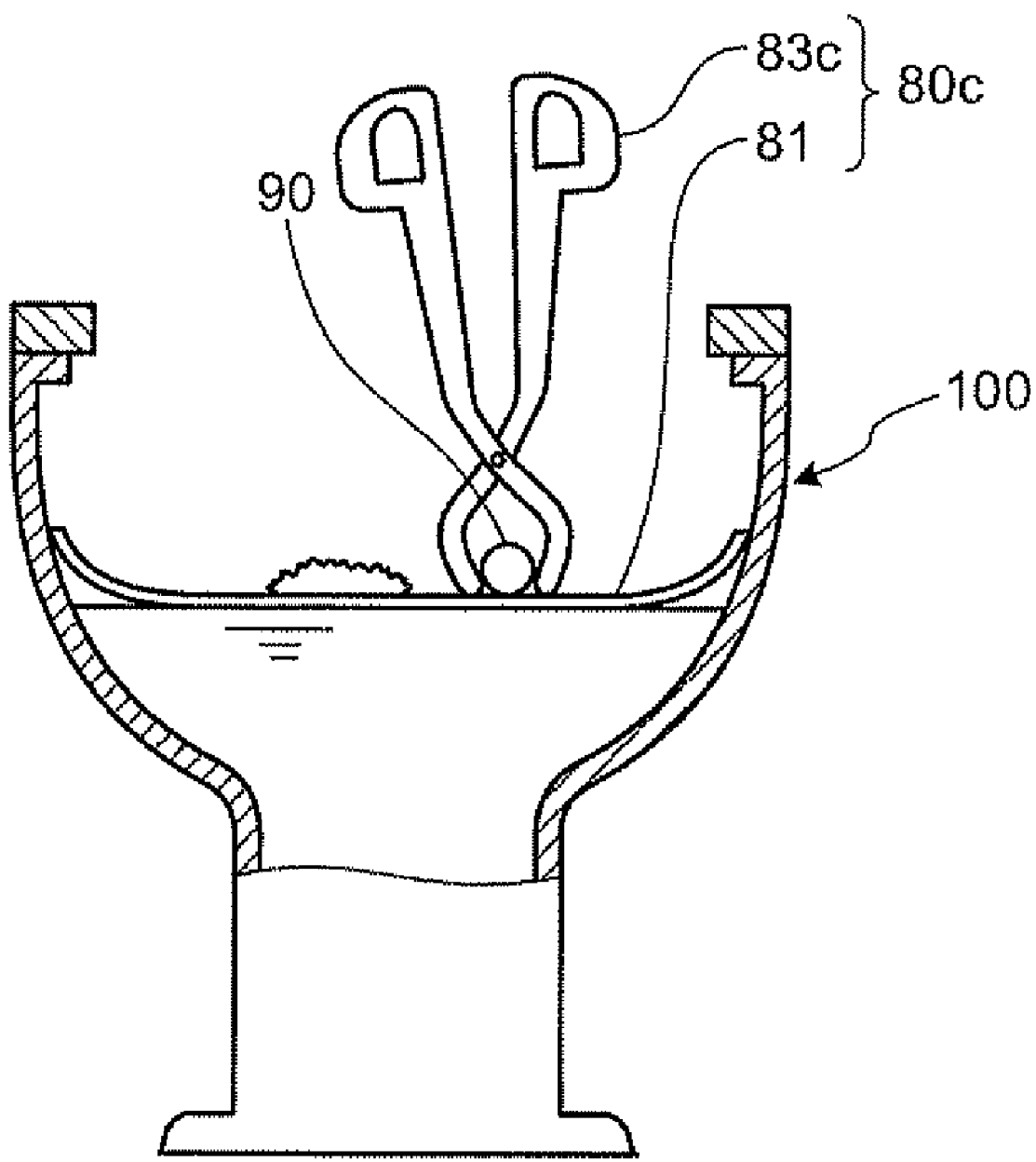
FIG. 25 is a diagram of a retriever for a capsule endoscope according to a variation.

The gripping member 83 is not limited to the tweezers. FIG. 25 is a retriever 80c for the capsule medical apparatus according to the present variation. As shown in FIG. 25, the retriever 80c may include a water-soluble sheet 81, and a gripping member 83c realized by tongs. Similarly to the fifth embodiment, the stool discharged onto the water-soluble sheet 81 is broken by the gripping member 83c realized by tongs, the found capsule medical apparatus 90 is gripped and retrieved by the gripping member 83c.

According to the in-vivo image acquiring apparatus, the in-vivo image receiving apparatus, and the in-vivo image acquiring system according to the embodiments, the light-control information for a control of light-control determined based on the brightness of the acquired image information can be easily acquired as information from which the distance between the in-vivo image acquiring apparatus and the wall surface of organs which are the subjects for the image information to be acquired by the in-vivo image acquiring apparatus can be estimated. Then, the light-control amount information can be wirelessly transmitted along with the image information acquired by the imaging unit. Accordingly, for example, an external apparatus can divide, based on the light-control amount information, the acquired image information to those which are captured when the in-vivo image acquiring apparatus is close to the wall surface of organ, and those which are captured when the in-vivo image acquiring apparatus is away from the wall surface of organ. Based on the result of division, a control can be realized, for example, where only the image information captured at a position close to the wall surface of organ is displayed, and the image information captured at a position away from the wall surface of organ is not displayed. Therefore, the image information which needs to be checked for the screening test and the like can be automatically extracted, whereby the observer can shorten observation time, and save burden on visually dividing the image information.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An in-vivo image acquiring apparatus, comprising:
an imaging unit that is introduced inside a subject to acquire image information of the subject;
an illuminating unit that illuminates a portion imaged by the imaging unit;
a transmission processing unit that performs a process to wirelessly transmit the image information acquired by the imaging unit to an external device; and
a light-control unit that determines light-control amount information based on brightness of the image information acquired by the imaging unit to perform a light control of the illuminating unit using the light-control amount information,
wherein the transmission processing unit performs a process to wirelessly transmit the light-control information used for the light control as information for estimating a distance between a front end of the in-vivo image acquiring apparatus and a wall surface of an organ of the subject, along with the image information acquired by the imaging unit.

2. An in-vivo image acquiring apparatus, comprising:
an imaging unit that is introduced inside a subject to acquire image information of the subject;
an illuminating unit that illuminates a portion imaged by the imaging unit;
a transmission processing unit that performs a process to wirelessly transmit the image information acquired by the imaging unit to an external device;
a light-control unit that determines light-control amount information based on brightness of the image information acquired by the imaging unit to perform a light control of the illuminating unit using the light-control amount information; and
a transmission determination unit that estimates a distance between a front end of the in-vivo image acquiring apparatus and a wall surface of an organ of the subject from the light-control amount information used for the light control, and the estimated distance, whether the process to transmit the image information acquired by the imaging unit is to be performed, wherein the transmission processing unit performs a process to wirelessly transmit the image information determined to be transmitted by the transmission determination unit.

3. An in-vivo image acquiring apparatus, comprising:
an imaging unit that is introduced inside a subject to acquire image information of the subject;
an illuminating unit that illuminates a portion imaged by the imaging unit;
a transmission processing unit that performs a process to wirelessly transmit the image information acquired by the imaging unit to an external device;
a light-control unit that determines light-control amount information based on brightness of the image information acquired by the imaging unit to perform a light control of the illuminating unit; and
an image processing unit that estimates a distance between a front end of the in-vivo image acquiring apparatus and a wall surface of an organ of the subject from the light-control amount information used for the light control, and performs, based on the estimated distance, a predetermined image processing on the image information acquired by the imaging unit.

4. The in-vivo image acquiring apparatus according to claim 3, wherein the image processing unit determines, based on the light-control amount information, whether the image information is to be compressed, and performs a compression process on the image information which is determined to be compressed.

5. The in-vivo image acquiring apparatus according to claim 3, wherein the image processing unit sets a compression rate based on the light-control amount information, and performs the compression process on the image information according to the set compression rate.

6. An in-vivo image receiving apparatus, receiving image information transmitted wirelessly from an in-vivo image acquiring apparatus that comprises an imaging unit that is introduced inside a subject to acquire image information of the subject;
an illuminating unit that illuminates a portion imaged by the imaging unit;
a transmission processing unit that performs a process to wirelessly transmit the image information acquired by the imaging unit to an external device,
a light-control unit that determines light-control amount information based on brightness of the image information acquired by the imaging unit to perform a light control of the illuminating unit using the light-control amount information, wherein the transmission processing unit performs a process to wirelessly transmit the light-control information used for the light control along with the image information acquired by the imaging unit, the in-vivo image receiving apparatus comprising:
a receiving unit that is arranged outside the subject, and receives the image information and the light-control information transmitted wirelessly from the in-vivo image acquiring apparatus; and
a display processing unit that estimates a distance between a front end of the in-vivo image acquiring apparatus and a wall surface of an organ of the subject from the light-control amount information received along with the image information by the receiving unit, and performs, based on the estimated distance, a process to display the image information.

7. The in-vivo image receiving apparatus according to claim 6, wherein the display processing unit determines, based on the estimated distance, whether the image information is to be displayed, and performs a process to display the image information which is determined to be displayed.

8. The in-vivo image receiving apparatus according to claim 6, wherein the display processing unit performs a process to sequentially switch and continuously display the image information received by the receiving unit, and changes, based on the estimated distance, display time of the image information.

9. An in-vivo image receiving apparatus for receiving image information transmitted wirelessly from an in-vivo image acquiring apparatus that comprises an imaging unit that is introduced inside a subject to acquire image information of the subject, an illuminating unit that illuminates a portion imaged by the imaging unit, a transmission processing unit that performs a process to wirelessly transmit the image information acquired by the imaging unit to an external device, a light-control unit that determines light-control amount information based on brightness of the image information acquired by the imaging unit to perform a light control of the illuminating unit using the light-control amount information, and a transmission determination unit that estimates a distance between a front end of the in-vivo image acquiring apparatus and a wall surface of an organ of the subject from the light-control amount information used for the light control, and determines, based on the estimated distance, whether the process to transmit the image information acquired by the imaging unit is to be performed, the transmission determination unit performing a process to wirelessly transmit the image information which is determined to be transmitted by the transmission determination unit, the in-vivo image receiving apparatus comprising:
a receiving unit that is arranged outside the subject, and receives the image information transmitted wirelessly from the in-vivo image acquiring apparatus; and
a display processing unit that performs a process to display the image information received by the receiving unit.

10. The in-vivo image receiving apparatus according to claim 9, wherein the display processing unit determines, based on the light-control amount information received along with the image information received by the receiving unit, whether the image information is to be displayed, and performs a process to display the image information which is determined to be displayed.

11. The in-vivo image receiving apparatus according to claim 9, wherein the display processing unit performs a process to sequentially switch and continuously display the image information received by the receiving unit, and changes, based on the light-control amount information received along with the image information, display time of the image information.

12. An in-vivo image receiving apparatus for receiving image information transmitted wirelessly from an in-vivo image acquiring apparatus that comprises an imaging unit that is introduced inside a subject to acquire image information of the subject, an illuminating unit that illuminates a portion imaged by the imaging unit, a transmission processing unit that performs a process to wirelessly transmit the image information acquired by the imaging unit to an external device, a light-control unit, which determines light-control amount information based on brightness of the image information acquired by the imaging unit to perform a light control of the illuminating unit, and an image processing unit, which estimates a distance between a front end of the in-vivo image acquiring apparatus and a wall surface of an organ of the subject from the light-control amount information used for the light control, and performs, based on the estimated distance, a predetermined image processing on the image information acquired by the imaging unit, the in-vivo image receiving apparatus comprising:
- a receiving unit that is arranged outside the subject, and receives the image information transmitted wirelessly from the in-vivo image acquiring apparatus; and
- a display processing unit, which performs a process to display the image information received by the receiving unit.

13. The in-vivo image receiving apparatus according to claim 12, wherein the display processing unit determines, based on the light-control amount information received along with the image information received by the receiving unit, whether the image information is to be displayed, and performs a process to display the image information which is determined to be displayed.

14. The in-vivo image receiving apparatus according to claim 12, wherein the display processing unit performs a process to sequentially switch and continuously display the image information received by the receiving unit, and changes, based on the light-control amount information received along with the image information, display time of the image information.

15. An in-vivo image acquiring system, comprising:
- an in-vivo image acquiring apparatus that comprises an imaging unit that is introduced inside a subject to acquire image information of the subject, an illuminating unit that illuminates a portion imaged by the imaging unit, a transmission processing unit that performs a process to wirelessly transmit the image information acquired by the imaging unit to an external device, a light-control unit, which determines light-control amount information based on brightness of the image information acquired by the imaging unit to perform a light control of the illuminating unit using the light-control amount information, the transmission processing unit performing a process to wirelessly transmit the light-control information used for the light control as information for estimating a distance between a front end of the in-vivo image acquiring apparatus and a wall surface of an organ of the subject, along with the image information acquired by the imaging unit;
- a receiving unit that is arranged outside the subject, and receives the image information and the light-control information transmitted wirelessly from the in-vivo image acquiring apparatus; and
- a display processing unit that estimates a distance between a front end of the in-vivo image acquiring apparatus and the wall surface of the organ of the subject from the light-control amount information received along with the image information by the receiving unit, and performs, based on the estimated distance, a process to display the image information.

16. An in-vivo image acquiring system, comprising:
- an in-vivo image acquiring apparatus that comprises an imaging unit that is introduced inside a subject to acquire image information of the subject, an illuminating unit that illuminates a portion imaged by the imaging unit, a transmission processing unit that performs a process to wirelessly transmit the image information acquired by the imaging unit to an external device, a light-control unit that determines light-control amount information based on brightness of the image information acquired by the imaging unit to perform a light control of the illuminating unit using the light-control amount information, and a transmission determination unit that estimates a distance between a front end of the in-vivo image acquiring apparatus and a wall surface of an organ of the subject from the light-control amount information used for the light control, and determines, based on the estimated distance, whether the process to transmit the image information acquired by the imaging unit is to be performed, the transmission determination unit performing a process to wirelessly transmit the image information which is determined to be transmitted by the transmission determination unit;
- a receiving unit that is arranged outside the subject, and receives the image information transmitted wirelessly from the in-vivo image acquiring apparatus; and
- a display processing unit that performs, a process to display the image information received by the receiving unit.

17. An in-vivo image acquiring system, comprising:
- an in-vivo image acquiring apparatus that comprises an imaging unit that is introduced inside a subject to acquire image information of the subject, an illuminating unit that illuminates a portion imaged by the imaging unit, a transmission processing unit that performs a process to wirelessly transmit the image information acquired by the imaging unit to an external device, a light-control unit that determines light-control amount information based on brightness of the image information acquired by the imaging unit to perform a light control of the illuminating unit, and an image processing unit, which estimates a distance between a front end of the in-vivo image acquiring apparatus and a wall surface of an organ of the subject from the light-control amount information used for the light control, and performs based on the estimated distance, a predetermined image processing on the image information acquired by the imaging unit;
- a receiving unit that is arranged outside the subject, and receives the image information transmitted wirelessly from the in-vivo image acquiring apparatus; and
- a display processing unit that performs a process to display the image information received by the receiving unit.

* * * * *